United States Patent [19]

Stapleton et al.

[11] Patent Number: 5,846,735
[45] Date of Patent: Dec. 8, 1998

[54] HEPATITIS C VIRUS FC-BINDING FUNCTION

[75] Inventors: Jack T. Stapleton, Iowa City, Iowa; Jian-Qiu Han, Shanghai, China; Douglas LaBrecque; Warren N. Schmidt, both of Iowa City, Iowa

[73] Assignee: University of Iowa Research Foundation, Iowa City, Iowa

[21] Appl. No.: 634,545

[22] Filed: Apr. 18, 1996

[51] Int. Cl.[6] .................. G01N 33/53; G01N 33/576; C07K 16/00; C07K 14/735

[52] U.S. Cl. .................. 435/7.1; 435/5; 435/7.72; 435/7.9; 435/7.92; 435/7.93; 435/960; 530/387.1; 530/387.3; 530/388.3; 530/389.1; 530/389.4; 530/391.1; 530/391.3; 530/866

[58] Field of Search .................. 435/5, 7.1, 7.72, 4357.9, 7.92, 7.93, 960; 530/387.1, 866, 387.3, 388.3, 389.1, 389.4, 391.1, 391.3

[56] References Cited

U.S. PATENT DOCUMENTS 5,350,671   9/1994   Houghton et al. .................. 435/5

OTHER PUBLICATIONS

Agnello et al., "A Role for Hepatitis C Virus Infection in Type II Cryoglobulinemia," *The New England Journal of Medicine*, 327(21):1490–1495, Nov. 1992.

Boubbard et al., "Hepatitis C Virus is Detected in a Monocyte/Macrophage Subpopulation of Peripheral Blood Monocuclear Cells of Infected Patients," *The J of Infectious Diseases*, 166:1276–1280, 1992.

Choo et al., "Isolation of a cDNA Clone Derived from a Blood–Borne Non–A, Non–B Viral Hepatitis Genome," *Science*, 244:359–362, Apr. 1989.

de Haas et al., "Fcγ Receptors of Phagocytes," *J Lab Clin Med*, 126:330–341, 1995.

Feinstone et al., "Inactivation of Hepatitis B Virus and Non–A, Non–B Hepatitis by Chloroform," *Infection and Immunity*, 41(2):816–821, Aug. 1983.

Gumber and Chopra, "Hepatitis C: A Multifaceted Disease," *Ann Intern Med.*, 126:615–620, 1995.

He et al., "Determining the Size of Non–A, Non–B Hepatitis Virus by Filtration," *The Journal of Infectious Diseases*, 156(4):636–640, Oct. 1987.

Hoke et al., "Protection Against Japanese Encephalitis by Inactivation Vaccines," *The New England Journal of Medicine*, 319(10):608–614, Sep. 1988.

Kuo et al., An Assay for Circulating Antibodies to a Major Etiologic Virus of Human Non–A, Non–B Hepatitis, *Science*, 244:362–364, Apr. 1989.

Levo et al., "Association Between Hepatitis B Virus and Essential Mixed Cryoglobulinemia," *The New England Journal of Medicine*, 296(26):1501–1504, Jun. 1977.

McFarlane et al., "Hepatitis C Virus Antibodies in Chronic Active Hepatitis: Pathogenetic Factor or False–Positive Result?" *Lancet*, 335:754–757, 1990.

Miller and Purcell, "Hepatitis C Virus Shares Amino Acid Sequence similarity with Pestiviruses and Flaviviruses as well as Members of Two Plant Virus Supergroups," *Proc. Natl. Acad. Sci. USA*, 87:2057–2061, Mar. 1990.

Miyamura et al., "Detection of Antibody Against Antigen Expressed by Molecularly Cloned Hepatitis C Virus cDNA: Application to Diagnosis and Blood Screening for Posttransfusion Hepatitis," *Proc. Natl. Acad. Sci. USA*, 87:983–987, Feb. 1990.

Müller et al., "Peripheral Blood Leukocytes Serve as a Possible Extrahepatic Site for Hepatitis C Virus Replication," *Journal of General Virology*, 74:669–676, 1993.

Nakatsuji et al., "Detection of chronic Hepatitis C Virus Infection by Four Diagnostic Systems: First–Generation and Second–Generation Enzyme–Linked Immunosorbent Assay, Second–Generation Recombinant Immunoblot Assay and Nested Polymerase Chain Reaction Analysis," *Hepatology*, 16(2):300–305, 1992.

Pascual et al., "Hepatitis C Virus in Patients wiht Cryoglobulinemia Type II," *The Journal of Infectious Diseases*, 162:569–570, 1990.

Prince et al., "Patterns and Prevalence of Hepatitis C Virus Infection in Posttransfusion Non–A, Non–B Hepatitis," *The Journal of Infectious Diseases*, 167:1296–1301, 1993.

Schmidt et al., "Direct Detection of Hepatitis C Virus (HCV) RNA from Whole Blood, and Comparison with HCV RNA in Plasma and Peripheral Blood Mononuclear Cells," *Journal of Medical Virology*, 47:153–160, 1995.

FIG. 1

Shimizu et al., "Correlation Between the Infectivity of Hepatitis C Virus In Vivo and Its Infectivity In Vitro," *Proc. Natl. Acad. Sci., USA*, 90:6037–6041, Jul. 1993.

Shimizu et al., Evidence for In Vitro Replication of Hepatitis C Virus Genome in a Human T–Cell Line, *Proc. Natl. Acad. Sci. USA*, 89:5477–5481, Jun. 1992.

Shimizu et al., "Hepatits C Virus: Detection of Intracellular Virus Particles by Electron Microscopy," *Hepatology*, 23(2):205–209, Feb. 1996.

Takamizawa et al., "Structure and Organization of the Hepatitis C Virus Genome Isolated from Human Carriers," *Jounral of Virology*, 65(3):1105–1113, Mar. 1991.

Weiner et al., "Detection of Hepatitis C Viral Sequences in Non–A, Non–B Hepatitis," *Lancet*, 335:1–3, 1990.

*Primary Examiner*—Michael P. Woodward
*Assistant Examiner*—Mary K. Zeman
*Attorney, Agent, or Firm*—Arnold, White & Durkee

[57] ABSTRACT

The present invention involves the detection and purification of Hepatitis C Virus (HCV). More particularly, the invention involves the exploitation of a newly discovered Fc-binding function in HCV to capture HCV from infected samples. This permits greatly simplified methods of diagnosis, improved methods of treatment and, in addition, the first opportunity to purify significant quantities of HCV.

20 Claims, 7 Drawing Sheets

HEPATITIS C VIRUS FC-BINDING FUNCTION

BACKGROUND OF THE INVENTION

1. Field of the Invention

The present invention relates generally to the field of virology and immunology, specifically, in the detection of Hepatitis C Virus (HCV). More particularly, the invention involves the use of immunoglobulins to bind HCV in HCV-infected samples. Even more specifically, the present invention provides methods for isolating or detecting HCV using the Fc fragment of immunoglobulin. These methods also permit the purification of HCV-contaminated samples.

2. Description of the Related Art

Hepatitis C Virus (HCV) is a major cause of chronic liver disease worldwide, and remains the most common cause of post-transfusion non-A, non-B (NANB) hepatitis. The genetic organization and biophysical characteristics of HCV are similar to viruses of Flavivirus and Pestivirus.

The Center for Disease Control and Prevention (CDC) in Atlanta estimate the incidence of acute hepatitis NANB to be 170,000 infections per year, of which approximately 127,000 are asymptomatic. At least 50% of HCV infections lead to chronic infection and subsequent liver disease. HCV also is associated with a variety of immune complex diseases. For example, HCV has been associated with essential mixed cryoglobulinemia, and membranoproliferative glomerulonephritis, although the mechanism by which HCV causes these diseases is not delineated. It has been speculated that chronic viral infection, in the presence of anti-viral antibodies, leads to immune complex deposition.

The molecular cloning of the HCV genome has facilitated a number of new approaches for determining HCV gene function, pathogenesis, diagnosis and molecular epidemiology. Physicochemical characterization of the virus, infectivity analysis, and genetic analysis of the genome indicate that HCV is a lipid enveloped flavilike/pestilike virus with a diameter of 30–60 nm. Equilibrium centrifugation studies show the density of infectious intact HCV virion to be <1.06 g/ml. However, because of the absent, or at best poor in vitro replication of the virus, the biological characteristics of this virus remain obscure.

Nevertheless, HCV has yet to be visualized by electron microscopy (EM) or immune EM (IEM) and there currently are no practical means of isolating HCV. A simple technique which would allow the removal of the virus from infected plasma would provide an important tool to be used in the isolation of HCV for various uses. In addition, the ability to remove essentially all of HCV from a sample would provide a means of purifying blood for transfusions. Thus, there remains a need for improved methods by which HCV can be isolated.

SUMMARY OF THE INVENTION

The present invention is designed to overcome the shortcomings of the prior art by providing improved compositions and methods for detecting and isolating HCV and for purifying blood or plasma samples infected with the virus.

In a first embodiment, there is provided a method of isolating Hepatitis C Virus (HCV) comprising the steps of (a) obtaining a sample; (b) contacting the sample with an Fc-containing polypeptide; and (c) collecting HCV bound to the Fc-containing polypeptide. The sample may be serum, plasma, liver or circulating blood cells. The Fc-containing polypeptide may be IgA, IgG, IgM, or an Fc fragment of an immunoglobulin, an preferably is Fc fragment of an immunoglobulin. The Fc-containing polypeptide may be derived from human, bovine, goat or murine immunoglobulin. The Fc-containing polypeptide is used at a concentration of 40 $\mu$g/ml polypeptide or at a concentration of at least 2 $\mu$g/5 $\mu$l volume. To effect release of the isolated HCV from the Fc-containing polypeptide, the bound HCV is heated, subjected to a change in pH or a change in ionic strength.

In another embodiment, there is provided a method of detecting HCV in a sample comprising the steps of (a) obtaining said sample from an individual; (b) contacting said sample with Fc-containing polypeptide; and (c) detecting HCV bound to said Fc-containing polypeptide. Again, the sample may be serum, plasma, liver or circulating blood cells. The Fc-containing polypeptide may be IgA, IgG, IgM, or an Fc fragment of an immunoglobulin, an preferably is Fc fragment of an immunoglobulin. The Fc-containing polypeptide may be derived from human, bovine, goat or murine immunoglobulin. The detecting may comprise the step of amplifying an HCV nucleic acid or contacting the bound HCV with an antibody that binds immunologically to HCV. For amplifying an RNA molecule, RT-PCR is the preferred method. For antibody detection, the antibody preferably is labeled with signal generating compound.

In yet another embodiment, there is provided a method for purifying blood or plasma containing HCV comprising the steps of (a) obtaining blood or plasma; (b) contacting said blood or plasma with an Fc-containing polypeptide; and (c) separating bound HCV from blood or plasma. The Fc-containing polypeptide preferably is bound to a support. The Fc-containing polypeptide may be IgA, IgG, IgM, or an Fc fragment of an immunoglobulin, an preferably is Fc fragment of an immunoglobulin. The Fc-containing polypeptide may be derived from human, bovine, goat or murine immunoglobulin.

In still yet another embodiment, there is provided purified HCV prepared by a method having the steps of (a) obtaining a sample comprising HCV; (b) contacting the sample with an Fc-containing polypeptide; and (c) collecting the HCV bound to the Fc-containing polypeptide.

In still yet another embodiment, there is provided a method of treating an individual infected with HCV comprising the step of administering an antigen composition comprising purified HCV, further treated to render the HCV non-infectious, the antigen composition being dispersed in a pharmaceutical carrier.

In still yet another embodiment, there is provided a method of inducing an immune response to HCV comprising the step of administering an antigen composition comprising purified HCV in a pharmaceutical carrier.

In still yet another embodiment, there is provided a method of treating an individual infected with HCV comprising the step of administering an antibody that binds immunologically to HCV, the antibody being dispersed in a pharmaceutical carrier.

In still yet another embodiment, there is provided a method of treating an individual infected with HCV comprising the steps of (a) removing blood from the individual; (b) contacting said blood with an Fc-containing polypeptide; (c) separating the blood from the Fc-containing polypeptide; (d) returning said blood to said individual; and (e) administering an antiviral compound to the individual. The antiviral compound preferably is IF$\alpha$.

In still yet another embodiment, there is provided a method of targeting a therapeutic or diagnostic compound to an HCV infected cell in an individual comprising the steps of (a) providing a conjugate comprising an Fc-containing polypeptide and the compound bound thereto; and (b) administering the conjugate to the individual.

In still yet another embodiment, there is provided a purified molecule prepared by a method comprising the steps of (a) obtaining a sample comprising HCV; (b) solubilizing said HCV; (c) contacting said sample with an Fc-containing polypeptide; and (d) collecting the molecule bound to said HCV bound to said Fc-containing polypeptide. The solubilizing may be accomplished by detergent treatment.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1:
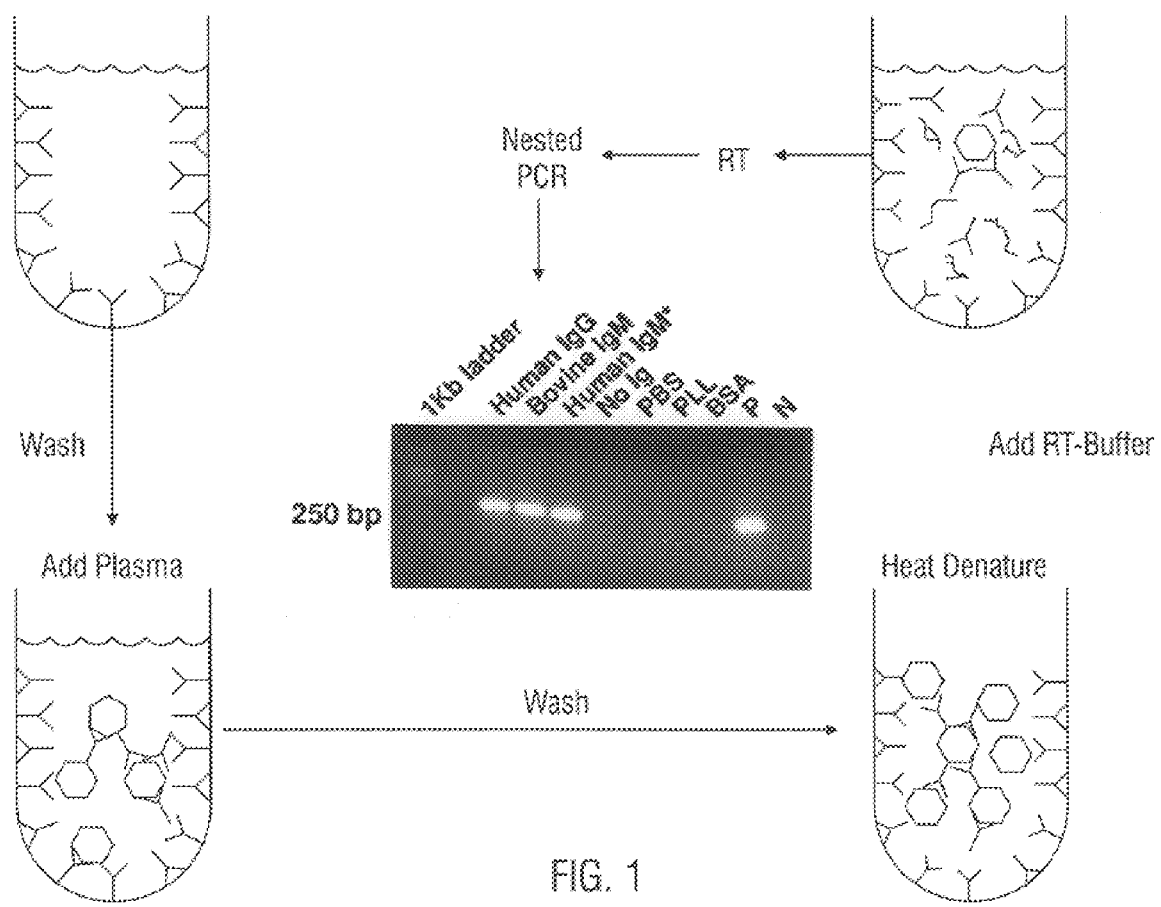
FIG. 1 Affinity-capture, reverse transcription-polymerase chain reaction (AC-PCR) method. Antibodies or control proteins (2 $\mu$g/50 $\mu$l) were applied to PCR tubes. Plasma was added, and following overnight incubation, reaction tubes were washed. Wash buffer was removed, and the tubes heated to denature virions (5 minutes, 95° C.). RT-PCR buffer was added, and RT-PCR carried out. The gel demonstrates results obtained when antibodies (human IgG, bovine IgM, human IgM [*=monoclonal]) or controls (no Ig=no coating, phosphate buffered saline [PBS], poly-L-Lysine [PLL], bovine serum albumin [BSA]) were used to coat the tubes. HCV antibody positive (P) and negative (N) plasma were used to isolate RNA for use as RT-PCR controls.

The present invention is based, in part, on the discovery that the Hepatitis C Virus (HCV) specifically binds to the Fc region of immunoglobulin. This observation provides new methods for the accurate and efficient diagnosis of HCV infection and for the purification of HCV-infected blood. The invention is described in detail below.

I. Hepatitis C Virus and Fc-Binding

Hepatitis viruses generally are defined as viruses which cause the symptoms of hepatitis. Hepatitis C Virus (HCV), a major causative agent of non-A, non-B hepatitis virus, is one of the three viruses known to cause the symptoms of hepatitis. Gumber and Chopra, 1995. The other viruses known to be responsible for hepatitis are hepatitis A virus and hepatitis B virus. The three hepatitis viruses belong to different families. For example, hepatitis A (infectious hepatitis) is a member of the *picornaviridae*, hepatitis B (serum hepatitis) belongs to the *hepadnaviridae*, and non-A, non-B hepatitis is thought to be caused by members of the *caliciviridae* (water-borne hepatitis), or *togaviridae* (post-transfusion hepatitis).

Non-A, non-B hepatitis (NANBH) represents greater than 90% of transfusion-associated hepatitis cases in the United States. Furthermore, up to 10% of transfusions have been estimated to result in NANBH. At least half of NANBH infections result in chronic hepatitis, which may result in cirrhosis in approximately 20% of cases.

While hepatitis B essentially affects only the liver of infected individuals, HCV is associated with a variety of immune complex diseases in addition to liver disease. Another unique characteristic of HCV is the frequency with which rheumatoid factor is detected in infected individuals. Rheumatoid factor is a complex of IgM antibody with specificity for the Fc portion of IgG that is found in many immune system-related, for example, rheumatoid arthritis.

Of patients with chronic HCV, over 70% are found to exhibit rheumatoid factor. Additionally, those patients with mixed essential cryoglobulinemia exhibit both rheumatoid factor and HCV RNA. Although the basis for the association of HCV and these diseases is not understood, it has been speculated that chronic viral infection, in the presence of anti-viral antibodies, leads to immune complex deposition. Pascual et al., 1990; Levo et al., 1977; Prince et al., 1995.

Interestingly, while autoimmune phenomena frequently accompany other chronic viral infections such as HIV or chronic hepatitis B, rheumatoid factor is not detected in nearly the same frequency as in chronic hepatitis C.

HCV has a positive sense RNA genome of approximately 9500 nucleotides which contains a single large open reading frame (ORF) encoding a polyprotein of 3010 amino acids. (2,3) It also has been shown that HCV is 30–60 nm in diameter and appears to possess an envelope made up of essential lipid. Choo et al., 1989; Miller et al., 1990. This protein is proteolytically processed by cellular and viral proteinases into at least nine structural (C, M and E) and non-structural end products (NS1, NS2, NS3, NS4a, NS4b and NS5).

The present inventors have discovered that HCV possesses an immunoglobulin Fc-binding function and that this binding is, surprisingly, independent of the isotype, species of origin or clonality of the antibody used. Additionally, it has been demonstrated that this binding is specific for the dimeric form of the Fc fragment of immunoglobulin, and presumably involves either or both of the highly conserved regions of Fc (region 3 or region 4). It also has been discovered that HCV binding to Fc is concentration dependent, and even small amounts of Ig result in capture of HCV RNA-containing material. This observation may be exploited in a variety of manners. For example, one may use Fc-containing molecules to purify HCV from samples. This is useful where the sample is to be used in a medical application, such as plasma for transfusions. Purified HCV also may be useful in various contexts. For example, purified HCV can be used to raise antibody for research or diagnostic purposes. It also may be used in vaccines for stimulating immune responses in vivo against HCV. The Fc-binding function also may be exploited in a diagnostic embodiment for determining HCV infection or contamination.

Immunoglobulins are a family of highly variable glycoproteins which bind specifically, and in some cases very tightly, to molecules foreign to the organism (i.e., antigens). The B cells of the immune system (B lymphocytes) are the only cells which produce immunoglobulins. Immunoglobulins are produced by the immune system of vertebrates and are essential for the prevention and resolution of infection by microorganisms. Immunoglobulins perform this function by recognizing and binding to particular molecular configurations on invading microorganisms and their products. One characteristic of immunoglobulins is that each type is able to bind only one or a small number of related molecular configurations Five classes of immunoglobulin have been defined in humans and the higher mammals. Those are IgG, IgM, IgA, IgD, and IgE. Additionally, humans have been found to have four subclasses of IgG and two subclasses of IgA. These immunoglobulins are present in all normal individuals and are referred to as isotypes. The type of heavy chain involved (termed $\gamma$, $\mu$, $\alpha$, $\delta$, and $\epsilon$ respectively) establishes the class of immunoglobulin. Each isotype is characterized by its amino acid sequence and is the product of a different gene segment. Additionally, two types of human immunoglobulin light chain were also defined by their distinct antigenicity and named kappa ($\kappa$) and lambda ($\lambda$). Of significance to the present invention is the discovery that HCV and HCV RNA binds to immunoglobulins regardless of their isotype or clonality.

When an Ig molecule is digested by papain to yield fragments, and these digestion products are dialyzed, protein crystals accounting for one-third of the original protein mass are produced. These crystals are termed the Fc fragment as they constitute the 'fragment crystallizable.' The fragments which account for two-thirds of the original protein mass bind antigen in a manner equivalent to the original molecule and are termed the Fab fragments as they were antigen binding.

Fc, being comprised of the carboxy-termini of two heavy chains, is dimeric in nature. The heavy chains are held together by interchain disulfide bonds. In addition, intrachain disulfide bonds add to the conformation of the Fc region. Carbohydrates are found attached to the Fc portion of immunoglobulin.

For the purposes of this application, an "Fc-containing" polypeptide is defined to include a polypeptide that contains sufficient sequences to effect binding to an Fc receptor. Obviously, this will include complete immunoglobulin molecules, including the mammalian IgM, IgG, IgE, IgD and IgA. It also includes the Fc portion of immunoglobulin that has been separated by proteolytic (papain, pepsin) or chemical cleavage or produced through genetic engineering and recombinant production. It also includes fragments of the Fc region of immunoglobulin, so long as those fragments are able to bind an Fc receptor.

Receptors specific for the Fc region of each of the antibody classes have been reported on a variety of cells. Examples of cells known to possess an Fc receptor are T cells, placental cells, and leukocytes. Although the Fc receptors on T cells and placental cells are poorly defined, those expressed on leukocytes are well defined and characterized. In addition, an Fc binding protein has been identified in herpes simplex virus. Prior to the present invention, however, HCV has not previously been known to contain an Fc receptor.

II. Purifying HCV From Samples

One of the serious problems stemming from HCV infection is the contamination of fluid samples, primarily blood, serum and plasma, that is transferred from one person to another. When such contaminated samples are used in transfusions, the individual to which the fluid is transferred will likely become infected. This is a particularly difficult situation because the transfusion recipient is likely already to have a compromised health situation. Another problem arises in the contamination of consumables, such as drinking water.

The present invention provides, in one embodiment, a method for the purification of fluid samples containing HCV. This purification relies upon the Fc-binding function of HCV. In its basic form, the method comprises contacting the HCV-containing fluid sample with an Fc-containing polypeptide. In this way, the HCV is brought into contact with the Fc-containing polypeptide, and binding of HCV to the Fc region is effected. Once this interaction has occurred, the fluid sample is separated from the Fc-bound HCV, thereby effecting purification.

The foregoing method may be employed in various fashions, but the preferred method involves an Fc-containing polypeptide bound to a support. For example, the Fc-containing polypeptide may be bound to a column or filter material and the HCV-containing fluid passed thereover. Most any commercially available column or filter may be used as this aspect of the method is not believed to be critical. Any HCV coming in contact with the support-bound Fc should bind the Fc-containing polypeptide, thereby being retained on the column. The flow through should contain only fluid depleted of HCV. It may be necessary to repeat the process one or more times to ensure that all the HCV is removed from the sample.

Another embodiment, where the Fc-containing polypeptide is bound to a support, involves the use of beads. The beads may be made of any suitable material, but preferably they are made of a material that separates easily from the sample fluid. For example, magnetic bead may be separated by subjecting the sample to an electromagnetic force. Other types of beads, depending on their density, may be separated from the sample fluid by centrifugation, e.g., density gradient centrifugation. By binding Fc-containing polypeptides to the surface of the beads, and then mixing the beads with the sample, HCV in the sample is brought into contact with the Fc-containing polypeptides. HCV bound to the beads is removed from the sample simply by removing the beads. Agitation (stirring, vortexing, etc.) may be performed to increase the accessibility of the HCV to the beads. And again, it may be desirable to repeat the process in order to completely remove the HCV.

It may be possible to reuse the support-bound Fc-containing polypeptides by releasing the HCV therefrom. Typically, receptor-ligand interactions are affected, for example, by changes in pH, ionic concentration and heat. By altering one of more of these parameters, it is possible to release the HCV bound to an Fc-containing polypeptide. Preferably, the condition is such that the structure of the Fc-containing polypeptide is not affected. It also may be important that the integrity of the HCV particle is not affected. This is important where, as described further below, it is desired to use the purified HCV as an antigen.

As indicated, preferred embodiments have the Fc-containing polypeptide bound to a support. The support may be any suitable material. For example, the polypeptide may be bound to polystyrene surfaces or to filters or gel materials. As stated above, any support material used in the preparation of columns may advantageously be employed. Beads of various compositions also may be used according the present invention. The Fc-containing polypeptide can be linked to a support in a variety of manners including both covalent and non-covalent fashions. In certain embodiments, it may be desired to space the Fc-containing polypeptide from the support by means of a spacer molecule. Such spacers are well know to those of skill in the art and preferably are bifunctional, i.e., have reactive groups at both ends.

As is discussed further, below, HCV purification will permit production of polyclonal and monoclonal antibodies specific for epitopes on HCV antigens. These antibodies, once produced, may be substituted for the Fc-containing polypeptides of the foregoing purification methods and in diagnostic techniques, discussed below. In other words, the binding specificity of such antibodies may be used to isolate and identify HCV from contaminated samples in much the same way that the Fc-containing polypeptides can be used. In some instances, such antibodies may, in fact, be more effective than Fc in effecting purification.

III. Purifying the Fc-binding Polypeptide of HCV

The present invention also encompasses the purification of a molecule, from HCV, that possesses an Fc-binding function. The purification process will be similar to that described above for whole HCV, at least to the extent that an Fc-containing polypeptide is employed to sequester the Fc-binding molecule. Again, the Fc-containing polypeptide preferably will be bound to a support and the molecule may be eluted from the Fc-containing polypeptide by altering the environment of the support (change in pH, ionic strength, etc.). The starting material may be unpurified HCV, but it may prove advantageous to first purify HCV away from a sample and then proceed with purification of the Fc-binding molecule.

The primary difference between the isolation of whole HCV and a distinct HCV molecule possessing an Fc-binding function will be the additional step of disrupting the HCV virion. Depending on the ultimate character of the Fc-binding molecule, this disruption may be accomplished in different fashions. The most typical disruption technique will involve detergent solubilization. A wide variety of different detergents, both ionic and non-ionic, may be used. For example, sodium dodecyl sulfate, sodium lauryl sulfate, Triton X-100, NP-40, deoxycholate or other bile acid may be employed. Alternatively, mechanical disruption may prove advantageous. This might involve the freeze-thawing, boiling or lyophilizing of an HCV-containing sample.

Following disruption, it also may be desirable to fractionate components prior to attempting to isolate the Fc-binding molecule. For example, one may separate components such as lipids and proteins from one another. Alternatively, one may want to separate membrane bound proteins from non-membrane bound proteins. One also may simply choose to destroy one or more fractions, for example, by the addition of enzymes such as proteases (destroy proteins) or lipases (destroy lipids). Those of skill in the art are well aware of how to achieve these goals.

Finally, the disrupted HCV-containing sample is contacted with an Fc-containing polypeptide, much in the manner described above. Because of the possibly harsh nature of the disruption, one should always employ an control where untreated HCV is used in parallel, thus insuring that the Fc-containing material is functioning properly and that the elution treatment that effects release of HCV (and the Fc-binding molecule) is successful.

IV. Producing Antibodies To Purified HCV

As a result of the purification of HCV-containing samples, described in the preceding section, there will be provided a source of purified HCV. Previously, isolation of HCV has been difficult, at best, and the ability to examine the HCV structure and constituents has been limited. One of the important benefits of having significant quantities of purified HCV is the ability to generate polyclonal and monoclonal antibodies. These antibodies may be used in immunodetection methods, immunopurification methods or in passive immunization against HCV.

Polyclonal antibodies are easily produced by immunizing a suitable host animal with HCV or an HCV protein. These antigens are normally administered with a pharmaceutical buffer or diluent, such as phosphate-buffered saline. Immunostimulatory agents such as priming agents, adjuvants or carriers may be employed as well. Sera is withdrawn using lethal (cardiac puncture; decapitation) or non-lethal drawing approaches.

Monoclonal antibodies (MAbs) may be readily prepared through use of well-known techniques, such as those exemplified in U.S. Pat. No. 4,196,265. Typically, this technique involves immunizing a suitable animal with a selected immunogen composition, e.g., purified or partially purified protein, synthetic protein or fragments thereof. The immunizing composition is administered in a manner effective to stimulate antibody producing cells. Rodents such as mice and rats are preferred animals, however, the use of rabbit, guinea pig, sheep or frog is possible. The use of rats may provide certain advantages, but mice are preferred, with the BALB/c mouse being most preferred as the most routinely used animal and one that generally gives a higher percentage of stable fusions. It may be desirable to include in the vaccine any of a number of different substances referred to as adjuvants, which are known to stimulate the appropriate portion of the immune system of the vaccinated animal. Suitable adjuvants for the vaccination of animals include, but are not limited to oil emulsions such as Freund's complete or incomplete adjuvant (not suitable for livestock use), Marcol 52:Montanide 888 (Marcol is a Trademark of Esso, Montanide is a Trademark of SEPPIC, Paris), squalane or squalene, Adjuvant 65 (containing peanut oil, mannide monooleate and aluminum monostearate), mineral gels such as aluminum hydroxide, aluminum phosphate, calcium phosphate and alum, surfactants such as hexadecylamine, octadecylamine, lysolecithin, dimethyldioctadecylammonium bromide, N,N-dioctadecyl-N,N'-bis(2-hydroxyethyl)-propanediamine, methoxyhexadecylglycerol and pluronic polyols, polyanions such as pyran, dextran sulfate, polyacrylic acid and carbopol, peptides and amino acids such as muramyl dipeptide, dimethylglycine, tuftsin and trehalose dimycolate.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of the animal with the highest antibody titer removed. Spleen lymphocytes are obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell line, generally one of the same species as the animal that was immunized. Myeloma cell lines suited for use in hybridoma-producing fusion procedures preferably are non-antibody-producing, have high fusion efficiency and enzyme deficiencies that render them incapable of growing in certain selective media which support the growth of only the desired fused cells, called "hybridomas."

Any one of a number of myeloma cells may be used and these are known to those of skill in the art. For example, where the immunized animal is a mouse, one may use P3-X63/Ag8, X63-Ag8.653, NS1/1.Ag 41, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell line is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1: 1, respectively, in the presence of an agent or agents (chemical or electrical) that promote the fusion of cell membranes. Fusion methods using Sendai virus have been described by Kohler & Milstein (1975; 1976), and those using polyethylene glycol (PEG), such as 37% (v/v) PEG, by Gefter et al. (1977). The use of electrically induced fusion methods is also appropriate.

Fusion procedures usually produce viable hybrids at low frequencies, about $1 \times 10^{-6}$ to $1 \times 10^{-8}$. This does not pose a problem, however, as the viable, fused hybrids are differentiated from the parental, unfused cells (particularly the unfused myeloma cells that would normally continue to divide indefinitely) by culture in a selective medium. The selective medium generally is one that contains an agent that blocks the de novo synthesis of nucleotides in the tissue culture media. Exemplary and preferred agents are aminopterin, methotrexate and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g, hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas arc selected. Typically, selection of hybridomas is performed by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas are then serially diluted and cloned into individual antibody-producing cell lines, which clones can then be propagated indefinitely to provide MAbs. The cell lines may be exploited for MAb production in two basic ways. A sample of the hybridoma can be injected, usually in the peritoneal cavity, into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Monoclonal antibodies of the present invention also include anti-idiotypic antibodies produced by methods well-known in the art. Monoclonal antibodies according to the present invention also may be monoclonal heteroconjugates, i.e., hybrids of two or more antibody molecules. In another embodiment, monoclonal antibodies according to the invention are chimeric monoclonal antibodies. In one approach, the chimeric monoclonal antibody is engineered by cloning recombinant DNA containing the promoter, leader, and variable-region sequences from a mouse antibody producing cell and the constant-region exons from a human antibody gene. The antibody encoded by such a recombinant gene is a mouse-human chimera. Its antibody specificity is determined by the variable region derived from mouse sequences. Its isotype, which is determined by the constant region, is derived from human DNA.

In another embodiment, monoclonal antibodies according to the present invention is a "humanized" monoclonal antibody, produced by techniques well-known in the art. That is, mouse complementary determining regions ("CDRs") are transferred from heavy and light V-chains of the mouse Ig into a human V-domain, followed by the replacement of some human residues in the framework regions of their murine counterparts. "Humanized" monoclonal antibodies in accordance with this invention are especially suitable for use in vivo diagnostic and therapeutic methods.

As stated above, the monoclonal antibodies and fragments thereof according to this invention can be multiplied according to in vitro and in vivo methods well-known in the art. Multiplication in vitro is carried out in suitable culture media such as Dulbecco's modified Eagle medium or RPMI 1640 medium, optionally replenished by a mammalian serum such as fetal calf serum or trace elements and growth-sustaining supplements, e.g., feeder cells, such as normal mouse peritoneal exudate cells, spleen cells, bone marrow macrophages or the like. In vitro production provides relatively pure antibody preparations and allows scale-up to give large amounts of the desired antibodies. Techniques for large scale hybridoma cultivation under tissue culture conditions are known in the art and include homogenous suspension culture, e.g., in an airlift reactor or in a continuous stirrer reactor or immobilized or entrapped cell culture.

Large amounts of the monoclonal antibody of the present invention also may be obtained by multiplying hybridoma cells in vivo. Cell clones are injected into mammals which are histocompatible with the parent cells, e.g., syngeneic mice, to cause growth of antibody-producing tumors. Optionally, the animals are primed with a hydrocarbon, especially oils such as Pristane (tetramethylpentadecane) prior to injection.

In accordance with the present invention, fragments of the monoclonal antibody of the invention can be obtained from monoclonal antibodies produced as described above, by methods which include digestion with enzymes such as pepsin or papain and/or cleavage of disulfide bonds by chemical reduction. Alternatively, monoclonal antibody fragments encompassed by the present invention can be synthesized using an automated peptide synthesizer, or they may be produced manually using techniques well known in the art.

The monoclonal conjugates of the present invention are prepared by methods known in the art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents, or by reaction with an isothiocyanate. Conjugates with metal chelates are similarly produced. Other moieties to which antibodies may be conjugated include radionuclides such as $^{3}H$, $^{125}I$, $^{131}I$ $^{32}P$, $^{35}S$, $^{14}C$, $^{51}Cr$, $^{36}Cl$, $^{57}Co$, $^{58}Co$, $^{59}Fe$, $^{75}Se$, $^{152}Eu$, and $^{99m}Tc$, are other useful labels which can be conjugated to antibodies. Radioactively labeled monoclonal antibodies of the present invention are produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99}m$ by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as $SNCl_2$, a buffer solution such as sodium-potassium phthalate solution, and the antibody.

V. HCV Vaccines

The present invention also provides, by virtue of purification of HCV, a meaningful approach to the treatment of HCV infection. By using purified HCV, or subunits thereof, it is possible to generate an immune response against the virus. The immune response, humoral or cellular or both, provides a defense mechanism against HCV infection.

A. Vaccines and Active Immunity

One of the strongest defenses against viral infection is the host's own immune system. In some instances, it may prove effective to "prime" the immune system so that the immune response against a virus is more rapid, more sensitive or more intense than it would otherwise be. By providing a potential host with a vaccine that stimulates the immune system in this manner, active immunity is generated. Active immunity is defined, for the purpose of this application, as the generation of an immune response in an animal for the purpose of protecting that animal from a an antigen that is associated with HCV infection.

In one form, it will be desired to provide a vaccine comprising whole HCV. Obviously, one of the problems with such an approach is that HCV is an infectious, disease causing agent. Thus, it will be necessary to inactivate the virus such that an active infection is not established. This may be effected by heating the virus to a sufficient temperature that the virus is no longer infectious. Formalin or other chemical fixation may be used to render the virus incapable of host cell infection. Instructive in this regard is the work on Japanese Encephalitis Virus (JEV). Hoke et al., *New Engl. J Med.* 319:608–614 (1988). The methods for producing JEV fixed vaccine may advantageously be applied to the production of an HCV fixed vaccine. Virus is treated with formalin (0.06 percent final concentration) at 4° C. for 60 days. Virus is then concentrated, subjected to sucrose-density-gradient centrifugation to purify the virus, filtered and lyophilized.

Alternatively, it may be desirable to break down whole HCV into molecular components. This can be accomplished by proteolytic or chemical treatment, by heating or freezing, by detergent solubilization, by sonication, or any other suitable method. The fragments thus generated may be used together, as a heterogeneous mixture, or they may be separated and used individually. For example, separation may be performed by chromatographic procedures, by size or charge.

The antigen composition further is prepared by mixing, preferably homogeneously mixing, at least one antigen with at least one pharmaceutically or veterinarally acceptable carrier, diluent, or excipient using standard methods of pharmaceutical or veterinary preparation. In preferred embodiments of the invention, the animals to be immunized are mammals such as cats, dogs, horses and, more particularly, humans, although there is no limitation other than that the subject be capable of mounting an immune response of some kind.

The immunogenicity of HCV, the HCV antigens or fragments thereof may vary and, therefore, it may be desirable to couple the immunogen to a carrier molecule. Exemplary carriers are keyhole limpet hemocyanin (KLH) and human serum albumin. It also may be desirable to include in the vaccine any of a number of different substances referred to as adjuvants, which are known to stimulate the appropriate portion of the immune system of the vaccinated animal. Suitable adjuvants for the vaccination of animals include, but are not limited to oil emulsions such as Freund's complete or incomplete adjuvant (not suitable for livestock use), Marcol 52:Montanide 888 (Marcol is a Trademark of Esso, Montanide is a Trademark of SEPPIC, Paris), squalane or squalene, Adjuvant 65 (containing peanut oil, mannide monooleate and aluminum monostearate), mineral gels such as aluminum hydroxide, aluminum phosphate, calcium phosphate and alum, surfactants such as hexadecylamine, octadecylamine, lysolecithin, dimethyldioctadecylammonium bromide, N,N-dioctadecyl-N,N'- bis(2-hydroxyethyl)-propanediamine, methoxyhexadecylglycerol and pluronic polyols, polyanions such as pyran, dextran sulfate, polyacrylic acid and carbopol, peptides and amino acids such as muramyl dipeptide, dimethylglycine, tuftsin and trehalose dimycolate.

The antigen preparations of the present invention also can be administered following incorporation into liposomes or other micro-carriers, or after conjugation to polysaccharides, proteins or polymers or in combination with Quil-A to form "iscoms" (immunostimulating complexes). These complexes can serve to reduce the toxicity of the antigen, delay its clearance from the host and improve the immune response by acting as an adjuvant. Other adjuvants suitable for use in the present invention include INF, IL-2, IL-4, IL-8 and other immunostimulatory compounds. Further, conjugates comprising the immunogen together with an integral membrane protein of prokaryotic origin, such as TraT (see PCT/AU87/00107) may prove advantageous.

Routes of administration, dosages to be administered, and frequency of injections are all factors which can be optimized using ordinary skill in the art. The antigen composition may be administered intravenously, subcutaneously, intranasally, orally, intramuscularly, urethrally, vaginally, rectally, topically, mucosally or via any other desired route. Of particular interest will be parenteral and mucosal routes.

Typically, the initial vaccination is followed some weeks later by one or more "booster" vaccinations, the net effect of which is the production of vigorous cellular and humoral immune response. The need for, or the appropriate timing of, subsequent boosters can be evaluated by measuring the immune response of the subject following each immunization. Animals would generally require two vaccinations 1–18 weeks apart, and additional vaccinations annually or more frequently as desired.

B. Passive Immunity

Passive immunity is defined, for the purposes of this application, as the transfer to an organism of an immune response effector that was generated in another organism. The classic example of establishing passive immunity is to transfer antibodies produced in one organism into a second, immunologically compatible animal. By "immunologically compatible," it is meant that the antibody can perform at least some of its immune functions in the new host animal. More recently, as a better understanding of cellular immune functions has evolved, it has become possible to accomplish passive immunity by transferring other effectors, such as certain kinds of lymphocytes, including cytotoxic and helper T cells, NK cells and other immune effector cells. The present invention contemplates both of these approaches.

Antibodies, antisera and immune effector cells are raised using reandard vaccination regimes in appropriate animals, as discussed above. The primary animal is vaccinated with a preparation of purified HCV or an HCV antigen according to the present invention, with or without an adjuvant, to generate an immune response. The immune response may be monitored, for example, by measurement of the levels of antibodies produced, using standard ELISA methods.

Once an adequate immune response has been generated, immune effector cells can be collected on a regular basis, usually from blood draws. The antibody fraction can be purified from the blood by standard means, e.g., by protein A or protein G chromatography. In an alternative preferred embodiment, monoclonal antibody-producing hybridomas are prepared by standard means (Coligan et al., 1991). Monoclonal antibodies are then prepared from the hybridoma cells by standard means. If the primary host's monoclonal antibodies are not compatible with the animal to be treated, it is possible that genetic engineering of the cells can be employed to modify the antibody to be tolerated by the animal to be treated. In the human context, murine antibodies, for example, may be "humanized" in this fashion.

Antibodies, antisera or immune effector cells, prepared as set forth above, are injected into hosts to provide passive immunity against viral infection. For example, an antibody composition is prepared by mixing, preferably homogeneously mixing, at least one antibody with at least one pharmaceutically or veterinarally acceptable carrier, diluent, or excipient using standard methods of pharmaceutical or veterinary preparation. The amount of antibody required to produce a single dosage form will vary depending upon the individual to be treated and the particular mode of administration. The specific dose level for any particular individual will depend upon a variety of factors including the age, body weight, general health, sex, and diet of the individual, time of administration, route of administration, rate of excretion, drug combination and the severity of the microbial infestation.

The antibody composition may be administered intravenously, subcutaneously, intranasally, orally, intramuscularly, vaginally, rectally, topically or via any other desired route. Repeated dosings may be necessary and will vary, for example, depending on the clinical setting, the particular microbe, the condition of the patient and the use of other therapies.

C. Augmenting Current Therapies

The current therapy for nonA-nonB hepatitis is treatment with IFα. The typical treatment regimen comprising intramuscular or subcutaneous injection of 3 million units of IFα three times a weeks for six months; double this dose it is a refractory patient. It has been shown, however, that the response rate is inversely proportional to the amount of HCV in the plasma. Thus, it is envisioned that the ability to reduce virus burden will greatly improve the results of conventional drug therapy directed against HCV. Though IFα is preferred, any suitable antiviral may be employed.

According to this embodiment, prior to treatment, a patient would be subjected to a blood purification process. The process would comprise filtration of the patient's blood by a system having Fc-containing polypeptides in sufficient quantities to remove substantially all of the circulating HCV from the blood. The blood would then be returned to the patient, at which time the IFα treatment would be commenced.

The filtration apparatus would comprise a means for withdrawing and reintroducing the blood to and from the patient. This could be accomplished by modifying standard blood drawing apparati such as needles and heparin coated tubing. Other commercial blood filtration units are available, for example, those use in blood dialysis or plasmaphoresis, could easily be modified for the present invention.

The blood would be circulated through the systems by means of peristaltic pumps or other suitable means. At some point in the system, the blood is contacted with Fc-containing polypeptides, preferably bound to a support. The support may be in the form of a cartridge that can be replaced with each use. Alternatively, the binding of HCV to the Fc-containing polypeptides may be reversed, as described above, thereby permitting reuse of the support.

D. Cell Targeting

The expression of an Fc binding function on HCV particles raises the possibility that such a function may be found on the surface of infected cells as well. If this is the case, it is possible that this function can be targeted by using Fc-containing polypeptides. In this way, it is possible to specifically target HCV-infected cells with either anti-HCV drugs, diagnostic reagents, toxins that will eliminate the infected cell, or antisense molecules that will specifically inhibit HCV transcription or translation.

For example, because of the side effects that systemic drug therapy often induces, it is preferred to target specific cells rather than subject the entire patient to the treatment. This can be accomplished according to the present invention by conjugating the therapeutic drug to an Fc-containing polypeptide. The conjugation may be direct or indirect, the latter method employing a linking agent. In preferred embodiments, the linkage would be cleaved after a period of time sufficient to target the conjugate to cells that bind Fc or, alternatively, it would be cleaved after internalization. IFα is a preferred drug in this regard.

It also may be desirable to kill infected cells outright. One way in which this may be accomplished is to target a toxin to HCV-infected cells using an Fc-containing polypeptide conjugated to a toxin. The conjugation may be via a direct or indirect linkage and may be cleavable. Suitable toxins include the ricin A chain, cholera toxin, α bungarotoxin, diptheria toxin or any other suitable natural or artificial toxin. Because other cells also express and Fc receptor, it is likely that such an approach would need require that such cells be protected from the effects of the toxin. This might be accomplished, for example, by fractionating a blood sample prior to treatment with toxin conjugate, and treating only that cell fraction that does not contain cells normally containing Fc receptors.

It also may be advantageous to use the Fc binding function of HCV-infected cells to target gene therapy thereto. For example, a vector construct encoding a therapeutic gene (HCV antisense gene, etc.) can be targeted specifically to HCV-infected cells using an Fc-containing polypeptide. Once taken up the cell, the gene is transcribed by the host cell's gene expression machinery. In the case of an antisense construct, the transcript will be expressed within the cell and hybridize to the target HCV sequence via base pairing, preventing or inhibiting transcription and or translation.

In the case of diagnostics, it may be desirable to identify particular cells that are expressing HCV antigens. Thus, the Fc-containing polypeptide will be conjugated to a signal generating compound. This compound may be a chromophore, a fluorophore, or it may emit radiation. Signal generating compounds suitable for this purpose are disclosed elsewhere in this document.

There is a considerable base of literature regarding the conjugation of proteins or proteins and nucleic acids, the use of immunoglobulins to target cells and the use of other receptor-ligand interactions to target therapeutics conjugates to cells. These technologies are very analogous to the instant situation and many of the same techniques will apply here. The following U.S. patents are incorporated by reference: U.S. Pat. No. 4,664,911, U.S. Pat. No. 4,935,465, and U.S. Pat. No. 5,116,944. The following references regarding use of receptor-mediated gene transfer also will be instructive: Wu and Wu, 1987.

VI. Detecting HCV Infection

Another aspect of the present invention involves the diagnosis of HCV infection by identifying the presence of HCV antigens or HCV RNA in samples such as blood, plasma, serum or liver or circulating blood cells. The invention utilizes the discovery that HCV specifically binds to the Fc region of an antibody molecule to effect this end. Because the Fc binding capabilities of HCV appear to be independent of the antibody isotype, species of origin or clonality, any Fc-containing polypeptides may be utilized in the methods of the present invention.

Previously, HCV has typically been detected through various assays. For example, Kuo et al. developed a recombinant-based assay for HCV antibodies. This group constructed an open reading frame encoding part of HCV and expressed it in yeast as a fusion polypeptide with superoxide dismutase (SOD). This fusion protein was then used to coat microtiter plates so that circulating HCV antibodies could be detected. Bound antigen was detected with a radioactive second antibody. Unfortunately, a high percentage of $HCV^+$patients are antibody negative, and assays relying on such assays may miss a much as ⅓ of infected individuals. Similarly, Choo et al., using a randomly primed cDNA library from NANBH positive plasma, were only able to detect significant amounts of the antibody using NANBH positive plasma antibodies. Serum from patients in the acute phase of post-transfusion NANBH exhibited negative results in the assay. Other groups have utilized RT-PCR methods to detect the presence of HCV RNA or of HCV antigen. These assays were reliant on cumbersome and time consuming RNA preparation steps.

The present invention seeks to avoid limitations in the prior art by utilizing the Fc-binding function of HCV to effectively concentrate and isolate the virus, hence, increasing the density and purity of the virus in a sample, thereby improving the threshold detection levels and minimizing time. The methods of the invention allow for the rapid and accurate detection of even minute amounts of the virus, down to 1–10 copies per 50 ml of sample.

The sample analyzed may be any sample that is suspected of containing an HCV-specific antigen, such as a biological sample (liver tissue section or specimen, a homogenized liver tissue extract, plasma, serum, blood, circulating blood cells, a blood cell membrane preparation, separated or purified forms) or any other sample, such as a food sample or water.

A. Polymerase Chain Reaction

In one embodiment, using a variation of polymerase chain reaction (PCR), the present inventors have detected HCV captured from infected samples on Fc-containing polypeptides. The particular approach, affinity-capture-reverse transcriptase PCR (AC-PCR), has previously been used to evaluate antibody-antigen interactions for pathogens. It is contemplated that other methods of amplification may be used in practicing the present invention. For example, ligase chain reaction (EPA 320 308), Qbeta Replicase (PCT/US87/00880), isothermal amplification, strand displacement amplification, modified priming amplification (PCT/US89/01025), cyclic single/double strand amplification (EPA 329 822), promoter hybridization amplification (PCT/WO89/06700), race amplification and one-sided.

Polymerase chain reaction is an extremely powerful tool for visualizing DNA molecules or single-copy genes of complex mixtures of genomic sequences. PCR is also useful for rapidly screening and/or sequencing inserts directly from aliquots of individual phage plaques or bacterial colonies. Numerous diverse PCR applications have been developed since its introduction.

PCR is an in vitro method of nucleic acid synthesis by which a particular segment of DNA can be specifically replicated. The method utilizes two oligonucleotide primers which flank the DNA fragment to be amplified. Further, the method comprises repeated cycles of heat denaturation of the DNA, annealing of the primers to their complementary sequences, and extension of the annealed primers with DNA polymerase. The oligonucleotide primers hybridize to opposite strands of the target sequence and are oriented so that DNA synthesis by the polymerase proceeds across the region between the primers. The successive cycles of amplification serve to double the amount of the target DNA synthesized in the previous cycle since the extension products created are also complementary to and capable of binding primers. Thus, the target fragment accumulates exponentially by approximately $2^n$, where n is the number of cycles of amplification performed.

Because HCV contains an RNA genome, and RNA is relatively unstable, it is desirable to convert the HCV RNA into a DNA form by reverse transcription. This so called RT-PCR method functions essentially like PCR with the exception that a preliminary conversion of RNA to cDNA is performed. The reverse transcription relies on an enzyme called reverse transcriptase. Through a relatively complicated series of events, a single-stranded RNA template provides for the generation of a single-stranded DNA template. Then, alternatively, RNA is degraded and a second strand of DNA is generated until a complete, double-stranded DNA copy of the original RNA template is created.

The assay functions as follows. First, a sample is brought into contact with an Fc-containing polypeptide. The polypeptide will be bound to a support, as described above for the purification process. The support typically will be a column, a tube, a dipstick, a bead or other suitable surface upon which the virus can adhere and then be separated from the remainder of the sample. Following separation, the viral genome will be released from the viral particle. This can be accomplished by heating the sample or dissolving the viral particle with detergents. Amplification of the sample can then be conducted without further purification.

PCR products may be detected in a variety of different fashions. For example, the sample may be electrophoresed on agarose gel and stained with ethidium bromide. Polyacrylamide gel electrophoresis also is contemplated. Alternatively, radioactively or fluorometrically labeled nucleotides may be utilized and the decay or emission measured following separation of unincorporated nucleotides.

B. Immunodetection Methods

As discussed above, the ability to purify HCV in large quantities provides the ability to generate a wide range of monoclonal antibodies against the virus. These new antibodies are likely to provide a variety of targets for immunodetection that previously were unavailable. Thus, in further embodiments of the present invention, standard methods for immunodetection of the HCV can be applied using these new reagents. The various immunodetection methods have been described in the scientific literature, such as, e.g., Nakamura et al. (1987), incorporated herein by reference.

In general, the immunodetection methods include obtaining a sample suspected of containing HCV and contacting the sample with an immunoglobulin specific for HCV or an Fc-containing polypeptide in accordance with the present invention, under conditions effective to allow the formation of immunecomplexes, which may then be detected with a second HCV-specific immunoglobulin or an Fc-containing polypeptide, and an antibody or binding agent specific for the bound HCV antibody.

Contacting the chosen sample with an antibody or Fc-containing polypeptide under conditions effective and for a period of time sufficient to allow the formation of immune complexes (primary immune complexes) generally only requires adding the antibody or Fc-containing polypeptide to the sample, typically at 4° C. After this time, the sample-antibody or sample-Fc composition will generally be washed to remove any non-specifically bound species, allowing only those molecules specifically bound within the primary immune complexes to be detected.

In general, the detection of immunocomplexes thus formed is well known in the art. This typically is accomplished by using a secondary antibody that binds to a second epitope on the antigen. The instant application also may employ an Fc-containing polypeptide as the secondary agent. Regardless, these methods are based upon the use of a label or marker attached to the secondary antibody. U.S. Patents concerning the use of such labels include U.S. Pat. Nos. 3,817,837; 3,850,752; 3,939,350; 3,996,345; 4,277,437; 4,275,149; and 4,366,241, each incorporated herein by reference. In addition, secondary agents may be directed against the bound antibody instead. Again, the conditions and period of time used are those sufficient to allow the formation of secondary immune complexes. The secondary immune complexes are then generally washed to remove any non-specifically bound labeled secondary antibodies or Fc-containing polypeptides, and the remaining label in the secondary immune complexes is then detected. The anti-HCV antibody, Fc-containing polypeptide or anti-immunoglobulin antibody is linked to a detectable label according to standard methodology, as described in the previously listed patents.

Immunoassays encompassed by the present invention include, but are not limited to those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

In one exemplary ELISA, the antibodies or Fc-containing polypeptides of the invention are immobilized onto a selected surface exhibiting protein affinity, such as a well in a polystyrene microtiter plate. Then, a test composition suspected of containing the HCV antigen, such as a clinical sample, is added to the wells. After binding and washing to remove non-specifically bound immunecomplexes, the bound HCV antigen may be detected. Detection is generally achieved by the addition of another anti-HCV antibody or an Fc-containing polypeptide that is linked to a detectable label. This type of ELISA is a simple "sandwich ELISA". Detection may also be achieved by the addition of an labeled second anti-HCV antibody or Fc-containing polypeptide, followed by the addition of a third antibody that has binding affinity for the second anti-HCV antibody, with the third antibody being linked to a detectable label.

In another exemplary ELISA, the samples suspected of containing the HCV antigen are immobilized onto the well surface and then contacted with antibodies of the invention. After binding and washing to remove non-specifically bound immunecomplexes, the bound HCV antigens or Fc receptors are detected. Where the initial antibodies or Fc-containing polypeptides are linked to a detectable label, the immunecomplexes may be detected directly. Again, the immunecomplexes may be detected using a second antibody that has binding affinity for the first anti-HCV antibody or Fc-containing polypeptide, with the second antibody being linked to a detectable label.

Another ELISA in which the HCV is immobilized, involves the use of antibody competition in the detection. In this ELISA, labeled antibodies or Fc-containing polypeptides are added to the wells, allowed to bind, and detected by means of their label. The amount of HCV in an unknown sample is then determined by mixing the sample with the labeled antibodies or Fc-containing polypeptides before or during incubation with coated wells. The presence of HCV in the sample acts to reduce the amount of anti-HCV antibody or Fc-containing polypeptide available for binding to the well and thus reduces the ultimate signal. This is appropriate for detecting HCV antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immunecomplexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with non-reactive material to reduce background, and washing to remove unbound material, the immobilizing surface is contacted with the control HCV and/or clinical or biological sample to be tested under conditions in a manner conducive to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

"Under conditions in a manner conducive to allow immunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

VII. EXAMPLES

A. Example 1
Detection of HCV RNA Using Fc-Isolated Virus Particles

MATERIALS AND METHODS

Clinical Specimens: Patients attending the University of Iowa Liver Clinic who were HCV antibody positive and had documented chronic hepatitis provided blood samples for these studies. Plasma was separated by centrifugation (twice) at 600× g for 10 minutes. Plasma was either used fresh, or was stored at −70° C. prior to use. This study was approved by the University of Iowa Institutional Review Board, and informed consent was obtained.

Preparation of Antibodies: Human polyclonal IgG (Sigma, St. Louis, Mo.) or HCV antibody negative IgG purified by protein G chromatography from a patient with recent hepatitis A infection (30), goat anti-human IgG (Sigma), bovine IgM (Sigma), Fc and Fab fragments prepared by papain digestion of HCV antibody negative human IgG (both Lambda and Kappa light chains, Athens Research and Technology, Inc. Athens, Ga.) were used for these studies. Human anti-HCV peptide antibodies (IgM) were raised against a synthetic peptide representing the C-100 protein region of HCV using standard methods. This protein is one of the three recombinant HCV proteins used to detect HCV antibodies in commercial diagnostic tests. Previously characterized murine monoclonal anti-hepatitis A virus antibody (IgG2a) are described in Stapleton and Lemon, 1987.

To reduce the disulfide bond on IgG or Fc fragments of IgG, samples were incubated in b mercaptoethanol (b-ME, 0.4M) and urea (8M) overnight at 40° C. The reaction was stopped by iodoacetomide (0.8M) for 15 minutes at 17° C. The completeness of reduction was assessed by determining the relative molecular weight of reduced IgG or Fc fragments by non-reducing SDS-PAGE, and proteins were identified by Coomassie blue staining. Prior to applying reduced IgG or Fc fragments to tubes for antigen-capture RT-PCR (see below), samples were diluted 1:25 in carbonate buffer (final concentration: 320 mM urea, 16 mM b-ME, 32 mM iodoacetamide).

Affinity-Capture RT-PCR Method: 2 μg antibody or control protein in 50 μl carbonate buffer (pH 9.6) was applied to 0.2 ml polypropylene PCR tubes (MicroAmp, Perkin Elmer) for 4 hrs at 37° C. Tubes were washed three times with 100 μl washing buffer (20 mM Tris, pH 8.4, 75 mM KCl, 2.5 mM $MgCl_2$, 0.01% NP-40), and HCV antibody positive plasma (diluted 1:1 in plasma sample buffer [Phosphate buffered saline [PBS, pH 7.4], 0.02% Triton X-100, 0.1% BSA]) was added. Following overnight incubation at 4° C., tubes were washed 6 to 8 times with 100 μl of washing buffer with care taken to avoid cross-contamination. Following removal of the wash buffer, reaction tubes were heated to 95° C. for 5 minutes to denature virus and release HCV-RNA. RT-PCR buffer was added and samples were amplified using a previously described nested RT-PCR method. Schmidt et al., 1995. Following agarose gel electrophoresis, DNA products were detected by ethidium bromide staining. Control samples included RNA prepared from HCV antibody positive and negative plasma, and a no RNA template control (water). A summary of the affinity-capture RT-PCR (AC-PCR) method and a demonstration of typical data obtained are shown in FIG. 1.

Differential Flotation Centrifugation: 300 μl HCV antibody positive plasma was added to 8 ml of NaCl (1.063 g/ml) and centrifuged at 139,000× g for 22 hours at 14° C. as described by Hijikata et al., 1993. Following centrifugation, a 1 ml fraction was removed from the top of the gradient, 6 mls were removed from the middle, and the remaining 1.3 mls were removed from the bottom of the tube. Samples were stored at −70° C. prior to use in the AC-PCR method.

HCV-RNA Preparation: To prepare HCV RNA from plasma to serve as controls, 200 μl of HCV antibody positive plasma were added to 1.0 ml of Catrimox for RNA extraction as previously described. Schmidt et al., 1995.

RESULTS

The initial experiments were designed to determine if the HCV anti-peptide antibodies would "capture" HCV from plasma. When bovine serum albumin (BSA), PBS, carbonate buffer, or poly-L-lysine were sued to coat the tubes, no binding occurred. Thus, when the human anti-HCV IgM monoclonal antibodies bound to HCV-RNA containing material, it appeared to be a specific interaction. However, using all control antibody preparations, HCV-RNA containing material also was captured, suggesting either non-specific sticking of HCV-RNA containing material or binding of HCV to a conserved region on immunoglobulin.

Consequently, this interaction was characterized further. Table I demonstrates the ability of different antibodies and antibody fragments to bind to HCV-RNA containing material in plasma. HCV binding was independent of the antibody isotype (IgA, IgG, IgM), species of origin (human, bovine, goat, murine), antigen specificity or clonality (polyclonal or monoclonal). Binding was concentration dependent, generally 0.02 μg/tube or greater antibody was required to bind HCV. For most experiments, 2 μg in 50 μl volume was used to coat each tube. When 2 μg/50 μl volume non-immunoglobulin protein, such as BSA or poly-L-lysine was used to coat reaction tubes, HCV was not bound to the tubes. Similarly, when the tubes were incubated with PBS alone, HCV-RNA was not detected. The coating and washing conditions were critical to avoid non-specific sticking of HCV-RNA containing material. Once conditions were optimized, reproducible results were obtained (Table I and Table II). Plasma from several different patients was evaluated, and all HCV-RNA positive plasma tested thus far demonstrated similar results (Table II). Thus, this phenomena is not isolated to a specific patient.

TABLE I

BINDING OF HEPATITIS C VIRUS (HCV) RNA CONTAINING MATERIAL FROM PLASMA

| Antibody[1] | | Species | IG Class | HCV RNA Detected | Tested (%) |
|---|---|---|---|---|---|
| HCV-1B5-8 | MAb[2] | human | IgM | 13/15 | (87) |
| B-IgM | PAb | bovine | IgM | 29/32 | (91) |
| JC-IgG | PAb | human | IgG | 87/101 | (86) |
| Sigma IgG | PAb | human | IgG | 19/22 | (86) |
| α-gamma | PAb | goat | IgG | 5/5 | (100) |
| HAV-B5-B3 | MAb | Mouse | $IgG_{2A}$ | 5/6 | (83) |
| Fc fragment[3] | | human | | 31/32 | (97) |
| | | | Total | 189/213 | (89) |
| Control[1] | | | | | |
| Fab fragment | | human | — | 1/18 | (5.5) |
| BSA | | bovine | — | 1/29 | (3.4) |
| Poly-l-lysine | | — | — | 0/9 | (0) |
| PBS | | — | — | 0/5 | (0) |
| No coating | | — | — | 2/40 | (5) |
| | | Total | | 4/101 | (4) |

[1]Material used to coat reaction tubes (2 μg in 50 μl carbonate buffer)
[2]MAb = monoclonal PAb = polyclonal
[3]Fc from pooled human immunoglobulin

TABLE II

HEPATITIS C VIRUS (HCV) ANTIGEN CAPTURE -RT PCR USING DIFFERENT SUBJECT'S PLASMA

| | CAPTURE[2] | | | |
|---|---|---|---|---|
| Subject[1] | B-IgM | H-IgG | H-Fc | Control |
| 1 | 14/15[3] | 41/44 | 18/18 | 0/27 |
| 2 | ND | 45/56 | 12/12 | 2/11 |
| 3 | 4/4 | 11/11 | ND | 2/9 |
| 4 | 8/8 | 4/4 | ND | 0/5 |
| Total | 26/27 (96%) | 101/115 (88%) | 40/40 (100%) | 4/52 (2.7%) |

[1]Patients with chronic hepatitis C infection documented by antibody.
[2]B-Igm = bovine IgM, H-IgG = human polyclonal (HCV antibody negative) IgG, H-Fc = human Fc fragments, and BSA or PBS controls.
[3]Data presented as the number positive/number of tests.

The coating and washing used in the AC-PCR method were important for avoiding non-specific sticking of HCV RNA-containing material to the reaction tubes. For example, the optimal plasma dilution was 1:2 to 1:4 in PBS containing 0.02% Triton X-100. This appeared to improve detection of HCV RNA, presumably by decreasing Taq polymerase inhibitors present in the plasma. The concentration of Fc fragment or antibody required to bind HCV to the reaction tube also was important, as monoclonal antibody culture supernatants initially did not bind HCV RNA-containing material as reproducibly as purified Ig. Subsequently, this was determined to be related to low antibody concentration present in the culture supernatants. Using the conditions described above, reproducible results were obtained (Table I). Plasma from different patients was evaluated, and all HCV-RNA positive plasma tested thus far demonstrated similar results (Table II). Thus, this phenomena does not appear to be isolated to a specific HCV infected patient. In addition, binding of other viruses to Ig and Ig antibody fragments does not generally occur. For example, when hepatitis A virus (HAV) antibody positive IgG or HAV antibody negative IgG was used to coat reactions tubes, followed by HAV-specific RT-PCR, HAV RNA was only detected when an HAV specific antibody was used to coat the tubes.

Figure 2:
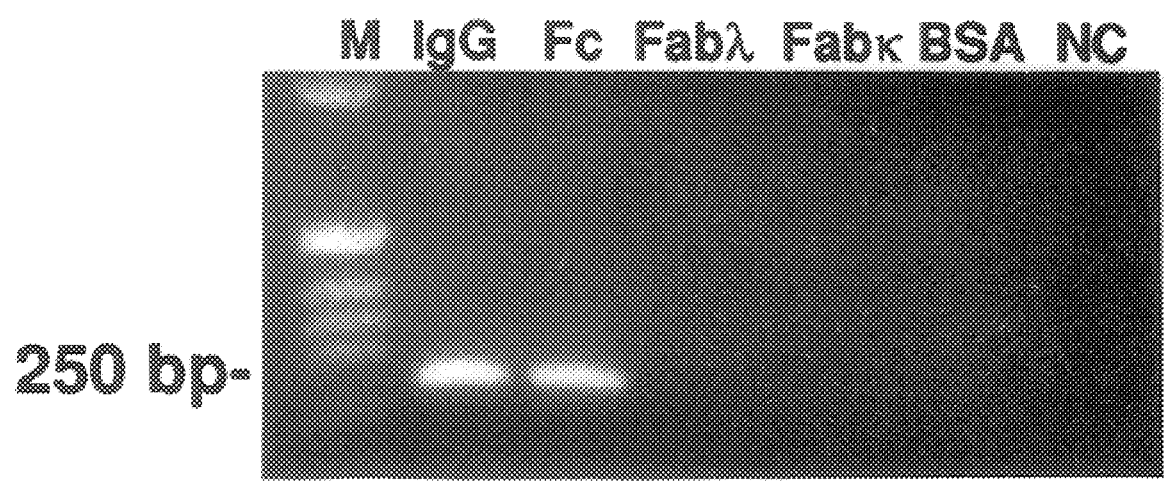
FIG. 2 Specific binding of HCV-RNA containing material by Affinity Capture-Reverse Transcription PCR. IgG, Fc, Fab$\lambda$, Fab$\kappa$, BSA and a PBS (no coating) control (NC) were used to coat reaction tubes, and HCV antibody positive plasma was added. AC-PCR was carried out and HCV RNA-containing material was captured by both IgG and Fc, but was not captured by Fab$\lambda$, Fab$\kappa$, BSA or the NC control.
Figure 3:
FIG. 3 Fc but not Fab fragments block binding HCV-RNA containing material to Fc fragments. The ability of buffer, Fc or Fab fragments to block the capture of HCV by IgG or Fc was assessed. Plasma was mixed with buffer or 44 $\mu$g of Fc or Fab for 3 hours at 37° C. followed by 3 hours at 4° C. prior to application to coated PCR tubes (coating material indicated at top of gel). M=DNA size marker. Blocking substance is indicated below the gel. B=buffer used for suspending IgG, Fc, or Fab fragments. Buffer did not block; however, Fc inhibited the ability of IgG and Fc to capture HCV-RNA containing material from plasma. Fab did not block capture by Fc.

To determine which part of the antibody molecules were binding to HCV-RNA containing material, purified human Fc and Fab fragments were used to coat reaction tubes (2 μg/tube). Human IgG Fc fragments captured HCV; however, Fab (both λ and κ) did not (FIG. 2, Table I). To verify the specificity of this binding, HCV-RNA containing plasma was incubated with Fc fragments for 3 hrs at 4° C. and 3 hrs in 37° C. prior to adding the mixture to IgG or Fc coated tubes. Following this incubation, tubes were washed and AC-PCR was carried out. Competing Fc fragments were added in two-fold increments, and HCV binding was competitively inhibited in a concentration dependent fashion. FIG. 3 demonstrates that Fc, but no Fab fragments compete for binding to Ig molecules.

Figure 4A:
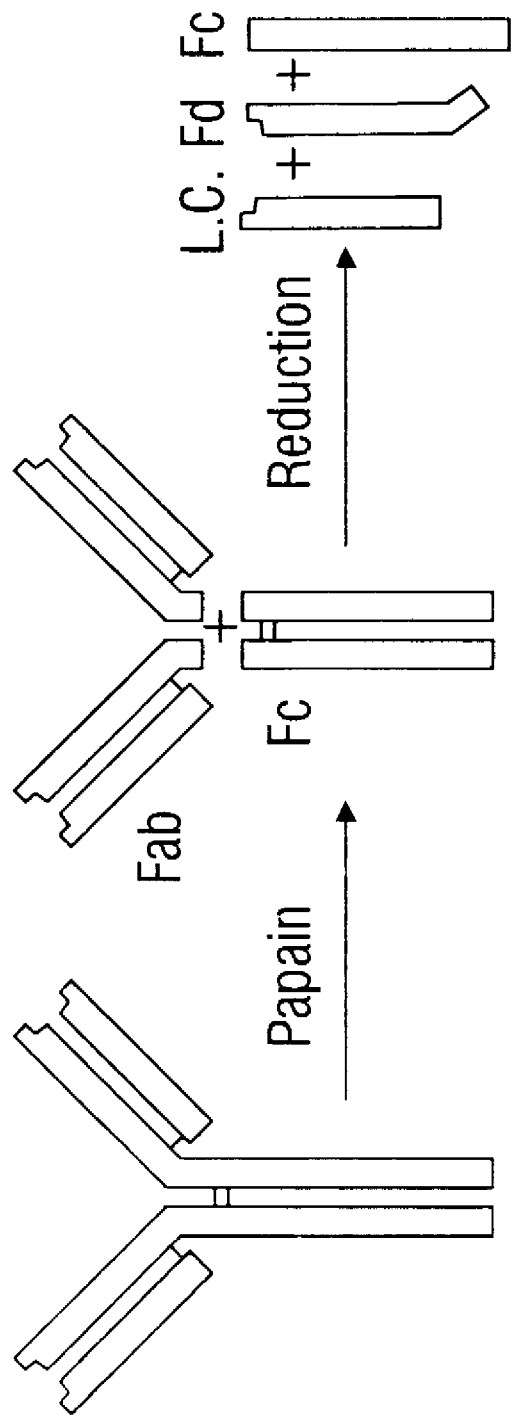
FIG. 4 Binding of hepatitis C virus RNA containing material to native and reduced Fc fragments. A. Schematic diagram demonstrating IgG molecule before and following papain digestion, and Fc denaturation by reduction of disulfide bonds. Following reduction of Fc and Fab'2 fragments, light chains (LC) and two heavy chain fragments (Fc, Fd) result. B. Fc fragments were incubated in 0.4M β-mercaptoethanol, 8M urea overnight (reduced Fc or FcR) or for <5 minutes (control Fc fragments or FcC). Iodoacetamide (0.8M) was added to prevent reformation of the disulfide bonds (both FcR and FcC). Relative molecular weights were determined by nonreducing SDS-PAGE of IgG, Fc, FcR, Fcc, and bovine serum albumin (BSA), and complete reduction of the FcR fragments was demonstrated. C. IgG, Fc, FcR, FcC, BSA and no coating (NC) controls were used to coat PCR tubes, and RT-PCR was carried out as described in FIG. 1.
Figure 4B:
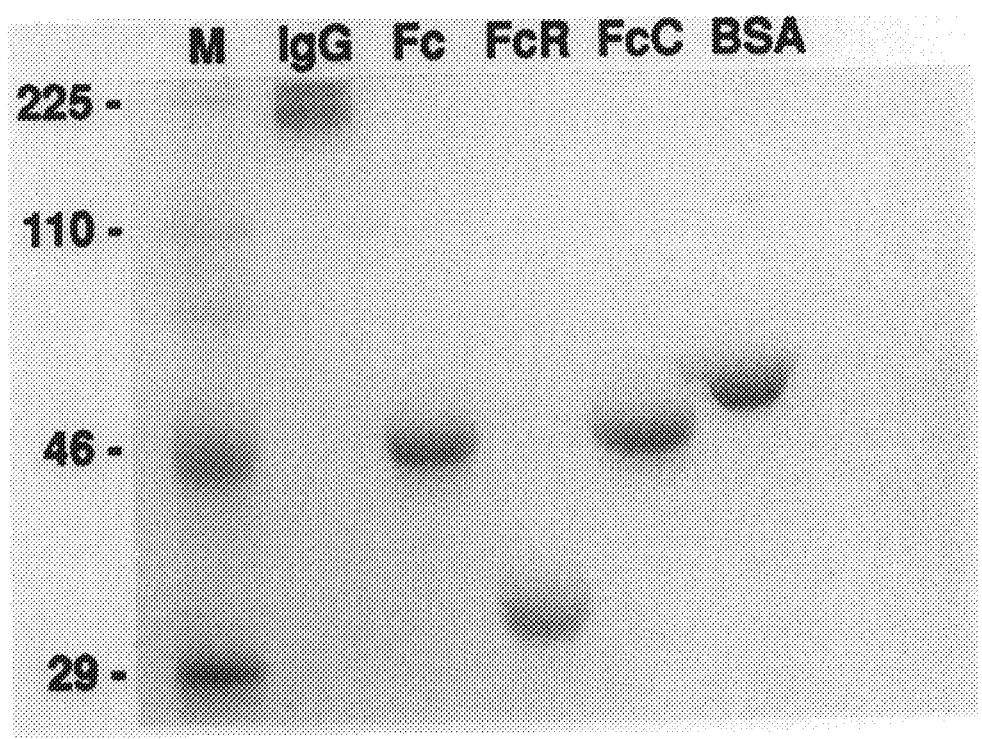
Figure 4C:
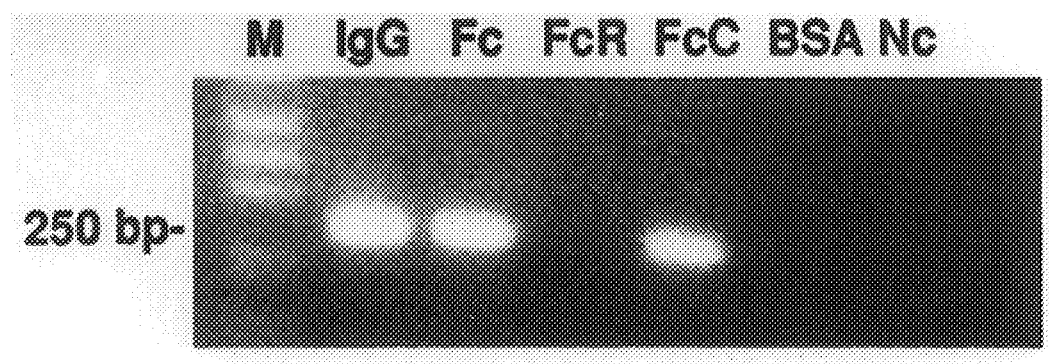

Native Fc fragments exist as dimers, connected by one or more disulfide bonds, depending on the antibody isotype (FIG. 4a). Since some Fc receptors require dimeric Fc for binding, we compared native and reduced Fc fragments for their ability to bind HCV RNA-containing material in plasma. The disulfide bond for purified Fc was reduced as described in the methods (FIG. 4a and 4b) and the resultant monomeric Fc fragment was used to coat reaction tubes (40 μg/ml). HCV binding was lost when reduced Fc fragments were used to coat the reaction tubes (FIG. 4c, lane FcR), indicating that the HCV-Fc interaction required a dimeric Fc molecule. The loss of binding was not due to the presence of urea, β-mercaptoethanol or iodoacetamide, as the addition of these reagents to Fc fragments (same concentrations) immediately before coating of the tubes did not result in loss of binding (control lanes FcC, FIG. 4b and 4c). Combined with the competition data obtained using Fc and Fab fragments, these studies demonstrate that HCV-RNA containing material specifically bound the Fc region of Ig molecules, and that the native, dimeric structure of the Fc fragment was required to interact with HCV.

To further characterize the HCV-RNA containing material in plasma that binds to Fc fragments, HCV-antibody complexes were separated from putative antibody-free HCV. This method was used to compare HCV populations for both infectivity in chimpanzees and immunoprecipitations with anti-human IgG, IgA and IgM antibodies. In this experiment, low infectivity HCV migrated to the bottom (more dense) fractions of saline density flotation gradients and could be immunoprecipitated. Conversely, highly infectious HCV was not precipitated by anti-human immunoglobulin and migrated to the upper (less dense) fraction. Consequently, the upper fraction represents putative "free" virus.

Figure 5A:
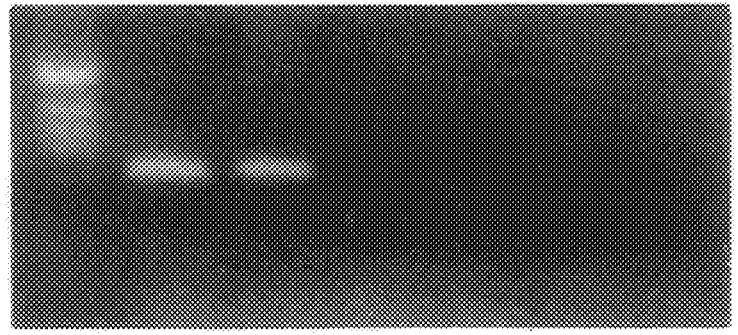
FIG. 5 Differential Flotation Sedimentation of hepatitis C virus (HCV) immune complexes and putative antibody-free HCV. Reaction tubes coated with 40 ug/ml IgG, Fc, Fab, staphylococcal protein A (SPA) or bovine serum albumin (BSA) were incubated with 50 $\mu$l aliquots of the top fraction (putative antibody-free virus, panel A) or the bottom fractions "HCV-immune-complexes" (panel B). IgG and Fc binding was demonstrated and Fab and BSA controls were uniformly negative. SPA only bound the bottom fraction, suggesting that Fc binding to the top fraction did not involve HCV-immune complexes.
Figure 5B:
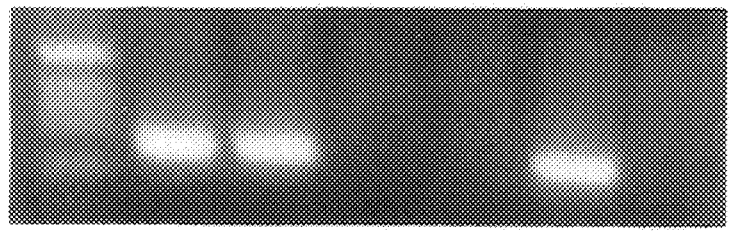

Using differential flotation centrifugation, putative free virus was separated from HCV-immune complexes and both components were evaluated for their ability to bind to antibody and antibody fragments. An additional control, Staphylococcal protein A was used to coat the reaction tubes. Protein A binds to the Fc region of most human immunoglobulin molecules, and it should also bind to HCV-antibody complexes found in plasma. FIG. 5 demonstrates results obtained when the upper fraction or lower fraction of saline density flotation gradients were applied to reaction tubes coated with IgG, Fc, Fab, bovine serum albumin or protein A. As predicted, the top (putative free HCV) bound to IgG and Fc; however, no HCV binding to Fab, BSA or protein A coated tubes was demonstrated. The lack of protein A binding suggested that this fragment was free of antibody. As expected, HCV-antibody complexes present in the bottom of the gradient bound to IgG, Fc and protein A coated tubes, while BSA and Fab coated tubes did not bind this fraction. These data suggest that the binding of HCV RNA-containing material to Fc involves a specific Fc binding domain on the virion, since both HCV-Ig and HCV plasma or cellular protein complexes would presumably migrate to the more dense fractions.

An alternative explanation for the foregoing results is that Fc is binding a plasma or cellular protein, released into plasma, which is complexed with HCV. To exclude this possibility, Ig or Fc coated tubes were incubated with plasma from an HCV antibody negative individual who has chronic hepatitis B virus infection for 16 h at 4° C. The tubes were washed, and HCV antibody positive plasma was added. AC-PCR was conducted as described above. This preincubation with HCV antibody negative plasma did not inhibit subsequent binding of HCV-RNA containing material to either Ig or Fc fragments, suggesting that plasma proteins are not involved in the HCV-Fc interaction.

In order to evaluate the sensitivity of this AC-PCR method, the amount of plasma required for a positive result was compared with the direct detection of HCV-RNA in the same plasma, as determined by catrimox RNA-isolation followed by RT-PCR Schmidt et al., 1995. HCV antibody positive plasma was serially diluted in two-fold increments prior to testing by AC-PCR. Results were compared with the RT-PCR results obtained using RNA purified from the same plasma. HCV-RNA in plasma was detected by AC-PCR when as little as 1 μl of plasma was applied, whereas HCV RNA from the same plasma (prepared by catrimox method) was detected in as little as 0.01 μl of plasma. Thus, the AC-PCR method appears slight less sensitive than direct detection of RNA from plasma. This suggests that not all HCV-RNA containing material is captured by the AC-PCR method, or that the lack of RNA extraction in the AC-PCR method may decrease the sensitivity of the method. Nonetheless, since no RNA extraction step is required, and all the reactions are done in a single tube, the AC-PCR method is a convenient way to identify HCV RNA.

B. EXAMPLE 2

Detection of HCV RNA in Chronic NANBNC Hepatitis Patients

MATERIALS AND METHODS

Reagents. Catrimox-14 (tetradecyltrimethylammonium oxalate) was kindly provided by Iowa Biotechnology (Oakdale, Iowa). Molecular biology grade pheno (Aramesco Inc., Solon, Ohio) and Taq DNA polymerase (Perkin-Elmer Cetus, Norwalk, Conn.), Maloney murine leukemia virus reverse transcriptase (RT) (Gibco/BRL Lift Technologies, Gaithersburg, Md.) and digoxigenin nucleic acid detection kits (Boehringer Mannheim Biochemical, Indianapolis, Ind.) were used in these studies.

Patients. Patients from the University of Iowa Liver Clinic were selected for this study following diagnosis with NANBNC chronic hepatitis. Maddrey, 1993; Alter et al., 1992; Schmidt et al., 1995. Other known causes for hepatitis (drugs, alcohol, iron or copper deposition, autoimmune liver disease, alpha-1-antitrypsin deficiency, Hepatitis B, C, EBV and CMV) were excluded by appropriate serologies. All were seronegative for HCV antibody by second generation immunoassays (EIA.2) (Abbott Labs, N. Chicago, Ill.) on at least tow samples obtained at least 6 months apart. RIBA II assays were kindly performed by the Hepatitis Reference Lab, Center for Disease Control and Prevention (Atlanta, Ga.). Where indicated, qualitative HCV-RNA analyses were performed by OncQuest (Santa Monica, Calif.).

Whole blood was collected, anticoagulated with acid citrate dextrose, kept on ice, and processed as soon as possible, usually within two hours of collection. Liver biopsies were evaluated by blinded slide review and were scored for grade and stage of chronic hepatitis and other inflammatory lesions. Desmet et al., 1994; Scheuer et al., 1991; Ludwig, 1993. The study was approved by the University of Iowa Institutional Review Board (Committee A) and informed consent was obtained.

Reverse Transcriptase Polymerase Chains Reaction Assays. Samples of whole blood or twice spun fresh plasma were mixed with 1.0 ml of Catrimox reagent, and RNA was prepared from the crude precipitate as previously described. Schmidt et al., 1995. Primers from the highly conserved 5' nontranslated region of HCV were used, and nested PCR was performed as previously described. Schmidt et al., 1995. Where indicated, non-structural region 3 (NS-3) primers, as described by Schlauder et al., 1992, were used in nested PCR reactions. The primers were (outer sense) 5'-GGCTATACCGGCGACTTCGA-3' (nucleotides 4668–4687); (nested sense) 5'-CACCATTGAGACAATCACGCTC-3' (nucleotides 4751–4772); (nested antisense) 5'-CGCCCAGTCTGTATAGCAGG-3' (nucleotides 5210–5229). The resultant NS-3 DNA product was 478 nucleotides in length. RT-PCR conditions were the same as described for RT-PCR using the 5' nontranslated region (ntr) primers. Schmidt et al., 1995. HCV RNA genotyping was performed using genotype-specific primers from both the core and NS-5 region. Okamoto et al., 1992; Chayama et al., 1993. PCR products were evaluated using either 1.6% or 2.4% agarose gel electrophoresis and ethidium bromide staining.

Dot Blots Using Digoxigenin-Labeled Nucleic Acid Detection. To confirm the identity of the RT-PCR products from patient samples, PCR products were hybridized with digoxigenin-labeled nucleic acid probes. Briefly, a digoxigenin-labeled DNA hybridization probe was prepared by amplifying known HCV sequences from a plasmid containing the HCV 5' nontranslated region (nucleotides 4–396). Brown et al., 1992. PCR products from patient samples or controls were applied to nylon membranes using a 2 $\mu$l sample volume. Hybridization and subsequent immunlogical detection were performed as recommended by the manufacturer (Boehringer Mannheim Biochemical).

RESULTS

Among 15 sequential NANBNC chronic hepatitis patients from our referral based liver clinic, HCV RNA was detected in the whole blood of 10 (patients A–J, 67%), whereas 5 patients had no detectable viral RNA (patients K–O) (Table III). When the plasma samples prepared from the same blood were tested, HCV RNA was detected in only 5 of these patients (A, D, E, H and J; Table III). Plasma samples were never positive for HCV RNA unless the corresponding WB sample was also positive. In addition, plasma HCV RNA detection was more variable than whole blood assays, as plasma from 3 of the 5 plasma positive patients were only intermittently positive for HCV RNA when tested on different dates (Table III). Moreover, for three patients (C, F and I), results of plasma RT-PCR obtained by commercial assay on the same blood sample were also negative, although our whole blood assay was positive (Table III).

All second generation HCV antibody immunoassays were negative on two or more occasions (Table IV). RIBA II assays were also performed, and only patient B was positive; no indeterminate results were observed. Interestingly, the single positive RIBA II test was carried out on a sample that was negative by EIA.2. This subject had two negative EIA tests over a three year period.

To determine if there were unusual HCV genotypes in these patients, which might explain the decreased frequency of antibody detection by standard EIA.2, the HCV genotypes were determined using established methodology (Okamoto et al., 1992; Chayama et al., 1993). Genotype I was the most common in our patients (Kuo et al., 1989), while 1 individual had type II, 2 had type III and 2 were type IV, a genotype that is relatively uncommon in the United States. Only one of the 10 HCV RNA positive patients could not be genotyped. This patient had 2 WB and 2 plasma samples positive for HCV RNA, and PCR amplification was accomplished from both the 5'-ntr and NS3 regions of the genome. These data confirm the specificity of our RT-PCR assay, as all positive samples demonstrated HCV RNA sequences representing at least two separate regions of the genome.

To further confirm the specificity and identity of the RT-PCR product generated from whole blood assays, dot-blot hybridizations were performed. Whole blood RT-PCR products from patients A–G showed specific hybridization even at high dilutions ($10^3$ to $10^4$, FIG. 2).

Similar findings were observed for patients H, I and J. No hybridization was detected for patient samples that showed no specific HCV product on agarose gels. Negative controls included calf thymus DNA, RT-PCR products using water as a template, and an HCV specific RT-PCR product generated from the NS-3 region of the virus. This PCR product is 478 nucleotides in length, and does contain the same HCV RNA sequences that are in the probe. An additional negative PCR control was a 748 nucleotide long PCR product from the HIV envelope gene generated from HIV proviral DNA using standard methods. All negative control DNA samples failed to hybridize with the HCV 5' ntr probe.

Table IV summarizes RT-PCR data from 52 samples from these 15 patients. Each plasma and whole blood RT-PCR result represents evaluation of an independent blood and plasma sample taken on different days, and not a replicate determination from the same RNA preparation. In patients with HCV RNA detected in either whole blood or plasma, 25/27 tests (93%) were positive using whole blood, whereas 7/27 plasma samples were positive. Chi square distribution analysis of these values demonstrated a highly significant difference between the whole blood and plasma assays for the ability to detect HCV RNA (Table IV).

Demographic, clinical laboratory analyses, and risk factors for chronic hepatitis were collected by review of the medical record (Table V). Although this study was retrospective, both HCV RNA positive and negative groups showed comparable ages, and the former group had a slightly longer mean follow-up time. In patients without cirrhosis, no significant differences were observed in the mean peak serum alanine aminotransferase or total bilirubin. As expected, patients with cirrhosis had higher levels of serum bilirubin and lower transaminase values than those without cirrhosis. Risk factors for chronic hepatitis in the HCV RNA positive and HCV RNA negative groups were also evaluated (Table V). Eighty percent of HCV-RNA negative and 50% of HCV RNA positive patients had no identifiable risk factors for HCV infection. Prior blood transfusion or a history of alcoholism were the most common risk factors for liver disease.

Liver biopsies were performed on 14 of the 15 patients and were obtained near the time of peak transaminase levels. A total of 16 biopsies were available for study, 9 in the HCV positive group and 7 in the HCV negative group. The histopathology was evaluated with the pathologist blinded in respect to the clinical and HCV RNA status of the patient. Histology was scored on a scale of 0–4 for histologic activity (grade) and fibrosis (stage) of chronic hepatitis (Desmet et al, 1994; Scheuer et aL, 1991). The presence of inflammatory cells, damaged hepatocytes, and other necroinflammatory cell types or lesions was also evaluated and scored on a scale of 0–3 (none, mild, moderate, severe). These results are summarized in Table VI. Histologic activity including the overall amount of portal infiltrate was significantly increased in biopsies obtained from HCV RNA positive patients. Significant increases were also seen in the number of ballooned cells and the degree of macrovesicular fatty change in the HCV RNA positive patients. In contrast, no significant differences were apparent between the two groups in the liver cells with a homogeneous appearing cytoplasm due to increased amounts of smooth endoplasmic reticulum, usually due to usage of a therapeutic drug (Popper, 1986). Interestingly, the number of induced hepatocytes was significantly increased in those who were HCV RNA negative when compared to those who were HCV RNA positive and suggests the possibility of an adverse drug effect.

TABLE III

Summary of whole blood and plasma HCV RNA determinations, genotype analysis, and immunoassay results for all study patients

| PATIENT | RT-PCR BLOOD | PLASMA | GENOTYPE | EIA.2 result/ # replicates | RIBA II |
|---|---|---|---|---|---|
| A. | + | + | I | –/2 | – |
|  | – | – |  |  |  |
|  | + | – |  |  |  |
| B. | + | – | IV | –/2 | + |
|  | + | – |  |  |  |
| C. | + | –* | I | –/2 | – |
|  | + | – |  |  |  |
|  | + | – |  |  |  |
|  | – | – |  |  |  |
| D. | + | – | I | –/3 | – |
|  | + | + |  |  |  |
| E. | + | – | I | –/2 | – |
|  | + | – |  |  |  |
|  | + | + |  |  |  |
| F. | + | –* | III | –/3 | – |
|  | + | – |  |  |  |
|  | + | – |  |  |  |
|  | + | – |  |  |  |
| G. | + | – | IV | –/2 | – |
|  | + | – |  |  |  |
| H. | + | + | [1]nt | –/3 | – |
|  | + | + |  |  |  |
| I. | + | –* | II | –/3 | – |
|  | + | – |  |  |  |
| J. | + | +Δ | III | –/3 | – |
|  | + | + |  |  |  |
| K. | – | – |  | –/3 | – |
| L. | – | – |  | –/3 | – |
|  | – | – |  |  |  |
| M. | – | – |  | –/6 | – |

TABLE III-continued

Summary of whole blood and plasma HCV RNA determinations, genotype analysis, and immunoassay results for all study patients

| PATIENT | RT-PCR BLOOD | PLASMA | GENOTYPE | EIA.2 result/ # replicates | RIBA II |
|---|---|---|---|---|---|
| N. | – | – |  | –/5 | – |
|  | – | – |  |  |  |
| O. | – | – |  | –/3 | – |

[1]nt = non-typeable
Each data point represents a separate, repeat RNA preparation and RT-PCR. Most of the blood specimens were collected on different clinic days.
(+) = HCV RNA detected.
* = Commercial RNA plasma negative
(–) = HCV RNA not detected
Δ = Commercial RNA plasma positive

TABLE IV

Comparison of whole blood HCV RNA detection with plasma HCV RNA detection in patients with unsuspected HCV infection

| HCV RNA | Positive | Negative | Total |
|---|---|---|---|
| Plasma | 7 | 19 | 26 |
| Blood | 24* | 2* | 26 |
| totals | 31 | 21 | 52 |

*Significantly different from plasma using Chi Square analysis (p <0.005). Data obtained on the 10 patients with positive HCV RNA assays were pooled (as listed in Table II) and compared statistically.

TABLE V

Demographic and clinical characteristics of 15 patients referred for NANBNC chronic hepatitis

| Characteristic | Whole Blood. HCV RNA + (N = 10) | Whole Blood. HCV RNA – (N = 5) |
|---|---|---|
| Mean age (years) | 53.1 +/– 3.9 | 46.8 +/– 2.4 |
| Sex M | 6 | 4 |
| F | 4 | 1 |
| Follow-up time (years) | 5.7 +/– 1.3 | 3.6 +/– 1.0 |
| [1]Peak total bilirubin. | | |
| (mg/dl) | | |
| without cirrhosis | 5.6 ± 2.3 | 3.5 ± 2.0 |
| with cirrhosis | 11.5 ± 4.2 | na |
| [1] Peak ALT (IU/L) | | |
| without cirrhosis | 449 ± 132.3 | 463.4 ± 145 |
| with cirrhosis | 63.3 ± 8.7 | na |
| Risk factors: | | |
| Injection drug use | 0 (0)* | 0 (0)* |
| [3]Occupational/Blood | | |
| product exposure | 1 (10) | 1 (20) |
| Blood transfusion | 2 (20) | 0 (0) |
| [4]Alcoholism | 2 (20) | 0 (0) |
| [5]Sexual | 0 (0) | 0 (0) |
| None | 5 (50) | 4 (80) |

[1]normal = 0.2–1.0 mg/dL
[2]alanine aminotransferase normal = 0–20 IU/L female and 0–35 IU/L male
[3]health care provider with exposure to blood products as a needle stick or excessive topical exposure
[4]defined as greater than 4 alcoholic beverages per day for greater than 20 years
[5]history of multiple sexual partners or prostitution
*values in parenthesis are percent of total

TABLE VI

Evaluation of liver biopsy findings in patients with serological Non-A, Non-B, Non-C chronic hepatitis

| Characteristic | Blood HCV RNA + N = 9 biopsies | Blood HCV RNA − N = 7 biopsies | [4]P Value |
|---|---|---|---|
| [1]Fibrosis | 2.64 ± .37 | 1.64 ± .33 | <.01 |
| [1]Activity | 2.28 ± .46 | 1.21 ± .53 | <.025 |
| [2]Portal infiltrate | 1.83 ± .34 | 0.53 ± .36 | <.025 |
| Lymphocytes | 1.39 ± .40 | 0.93 ± .36 | [A]n.s. |
| Plasma cells | 0.56 ± .36 | 0.50 ± .23 | n.s. |
| Neutrophils | 0.78 ± .34 | 0.57 ± .34 | n.s. |
| Acidophil bodies | 0.22 ± .21 | 0.14 ± .13 | n.s. |
| Eosinophils | 0.80 ± .41 | 0.29 ± .17 | n.s. |
| Ballooned cells | 1.17 ± .29 | 0.43 ± .27 | <.025 |
| Kupffer cells | | | |
| diffuse | 1.22 ± .30 | 0.72 ± .33 | n.s. |
| clusters | 0.83 ± .29 | 0.86 ± .37 | n.s. |
| [3]Induced hepatocytes | 0.44 ± .32 | 1.30 ± .48 | <.025 |
| Fatty changes | .889 ± .30 | .286 ± .17 | <.05 |

[1]Stage of fibrosis and grades of activity were scored on a scale of 0–4 (Scheuer, P. J.)
[2]Other characteristics were scored on a scale of 0–3 (none, mild, moderate, severe).
[1]Terminology as defined in reference 27.
[1]Significance assessed with paired student's t-test and pooled variances.
[A]n.s. = not significant

VIII. REFERENCES

The following references, to the extent that they provide exemplary procedural or other details supplementary to those set forth herein, are specifically incorporated herein by reference.

Aach et al, N. Engl. J. Med., 1991;325;1325–9.
Agnello et al, N. Engl. J. Med., 327; 1490–1495, 1992.
Alter, H. J., Vox Sangunis, 1994;67(S3): 19–24.
Alter, et al., N. Engl. J. Med., 1992;327:1899–1905.
Alter, M. J. & Sampliner, R. E., N. Engl. J. Med., 321; 1538–1540, 1989.
Bianco, C., "Hepatitis testing. Immunological investigations," 1995;24(1&2): 155–161.
Blight et al., Liver, 12;286–289, 1992.
Bouffard et al., J. Infect. Dis., 1992;166:1276–1280.
Bradley, et al., J. Infect., 1983;14:254–65.
Bradley et al., J. Infect. Dis., 148:6547–5649, 1983.
Bradley et al., Gastroenterology, 88:773–779, 1985.
Bradley, D. W., Transfusion Med. Rev., 5:93–102, 1992.
Bresters, et al., Vox. Sang., 1992;62:213–217.
Brown, D., "Diagnosis of hepatitis C," In: Zuckerman, A. J., Thomas, H. C., "Viral Hepatitis," Churchill Livingstone Press, 1993:283–301.
Brown et al., Nucleic Acids Res., 1992;20:5041–5045.
Bukh et al., J. Infect. Dis., 1993;168:1343–1348.
Buti, M., Jardi, R., Rodriguez-Frias, F., Quer, J., Esteban, R., Guardia, J., "Non-A, non-B, non-C, non-E acute hepatitis: Does it really exist?" In "Viral Hepatitis and Liver Disease," Tokyo, Springer-Verlag, 1994;77–79.
Chayama et al., Gastroenterology-Hepatology, 1993;8:150–156.
Chicheportiche et al., Virol. 1993;37:123–131.
Choo et al., Science, 244;359–362, 1989.
Coligan et al. (eds), Current Protocols in Immunology, John Wiley, New York, ch. 2.5, 1991.
Coombs et al., J. Clin. Microbiol., 31:1980–1986,1993.
Cuthbert, J. A., Clin. Microbiol. Reviews, 1994;7:505–532.
de Haas, et al., J. Lab. Clin. Med., 126:330–341, 1995.
Desmet et al., Hepatology, 1994;19:1513–1520.
Dine & Brahimi, Presse. Med., 22;269, 1993.
Feinstone et al., Infect. Immun., 41:816–821, 1983.
Fredman & Sela, J. Biol Chem., 241:2353, 1966.
Gabrielli et aL, Clin. Exp. Immunol., 1994;97:87–93.
Gefter et al. Somatic Cell Genet. 3:231–236 (1977).
Gumber and Chopra, Ann. Intern. Med., 1995; 123:615–620.
Hasemann & Capra, Immunoglobulins: Structure and Function., ed. Paul, W. E., 2: (9)209–233, 1989.
He et al., J. Infect. Dis., 156:636–640, 1987.
Hadziyannis et al., Program and abstracts of the 46th annual meeting of the American Association for the Study of Liver Diseases (Chicago), American Association for the Study of Liver Diseases, 1995:218A.
Hijikata., Proc. Natl. Acad. Sci. USA, 88;5547–5551, 1991.
Hijkata et al., Journal of Virology, 1993;67:1953–1958.
Hoke et al., New Engl. J. Med. 319:608–614, 1988.
Holodny et al., J. Clin. Invest., 1994;88:1755–1759.
Houghton et al, Hepatology, 14;381–388, 1991.
Jansen, et al., Proc. Natl. Acad. Sci. USA, 87:2867–2871, 1990.
Kohler & Milstein, Nature, 256:495–497, 1975.
Kohler & Milstein, Eur. J. Immunol, 6:511–519, 1976.
Kuo et al., Science, 1989;244:362–364.
Lee et al., Adv. Exp. Med. Bio., 1992;312:183–189.
Lenzi et al, Lancet, 335;258–259, 1990.
Levo et al, N. Engl. J. Med., 296; 1501–1504, 1977.
Linnen et al., Science, 1996;271 :505–508.
Ludwig, J., Gastroenterology, 1993;105:274–278.
Maddrey, W. C., Disease-a-Month, 1993;39(2): 53–125.
Magrin et al, J. Heptaol., 13;56–60, 1991.
McFarlane et al., Lancet, 335;754–757, 1990.
Michel et al, Lancet, 339;267–269, 1992.
Miller & Purcell, Proc. Natl. Acad. Sci., USA, 87;2057–2061, 1990.
Miyamura et al, PNAS, 87;983–987, 1989.
Muerhoff et al., Journal Virology, 1995 ;69(9): 5621–30.
Muller et al., J. Gen. Virol., 1993;74:669–676.
Nakatsuji et al., Hepatology, 1992; 16:300–305.
Okamoto et al., Virology, 1992;188:331–341.
Pascual et al., J. Infect. Dis., 162,569–570, 1990.
Popper, H., "Seminars in Liver Disease," 1986;6(3): 175–184.
Prince et al., J. Infect. Dis., 1995;167:1296–1301.
Quian et al., J. Hepatology, 1992;16:380–383.
Riezu-Boj et al., J. Hepatol, 13 S163, 1991.
Rosenfeld et al., J. Clin. Invest., 76:2317–2322, 1985.
Scheuer, P. J., Journal of Hepatology, 1991;13:372–374.
Schlauder et al., J. Virol. Meth., 1992;37:189–200.
Schmidt et al., Jour. Medical. Virol., 1995;47:153–160.
Schmidt et al., "Temporal Changes in the distribution of hepatitis C virus RNA in whole blood, plasma, and peripheral blood mononuclear cells during interferon treatment (abstract 252)," In: "Program and abstracts of the 46th annual meeting of the American Association for the Study of Liver Diseases (Chicago)," American Association for the Study of Liver Diseases, 1995:169A.
Schmidt et al., Triennial International Symposium on Viral Hepatitis and Liver Disease, Rome, Italy, 1996.
Simons et al., Proc. Natl. Acad. Sci., (USA) 1995;92(8): 3401–5.2.
Shimizu et al., Proc. Natl. Acad. Sci. USA, 89:5477–5481, 1992.
Shimizu et al., Proc. Natl. Acad. Sci. USA, 90:6037–6041, 1993.
Shimizu et al., Hepatology, 23:205–209, 1996.
Stapleton & Lemon, J. Virol., 61:491–498, 1987.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:1:

GGCTATACCG GCGACTTCGA                    20

( 2 ) INFORMATION FOR SEQ ID NO:2:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:2:

CACCATTGAG ACAATCACGC TC                    22

( 2 ) INFORMATION FOR SEQ ID NO:3:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:3:

CGCCCAGTCT GTATAGCAGG                    20

Sugitani et al., *Lancet,* 1992;339:1018–19.
Takamizawa et al., *J Virol.,* 65;1105–1113, 1991.
Tassopoulos et al., In "Viral Hepatitis and Liver Disease," Tokyo, Springer-Verlag, 1994;80–84.
Thomssen et al., *Med Microbiol Immunol,* 182:329–334, 1993.
Villa et al., *Jour. Hepatol.,* 1991;13:256–259.
Wilber, J. C., *J. Clin. Immunoassay,* 1993;16:204–207.
Wu & Wu, *J Biol. Chem.,* 262:4429–4432, 1987.
Yuasa et al., *J. Gen. Virol.,* 72:2021–2024, 1991.
Zanetti et al., *Lancet,* 1990;336:448.

What is claimed is:

1. A method of detecting HCV in a sample comprising the steps of:
    (a) obtaining said sample from an individual;
    (b) contacting said sample with Fc-containing polypeptide, said polypeptide lacking antigen binding specificity for HCV; and
    (c) detecting HCV bound to the Fc portion of said Fc-containing polypeptide.

2. The method of claim 1, wherein said sample is serum, plasma, liver, or circulating blood cells.

3. The method of claim 1, wherein said Fc-containing polypeptide is IgA, IgG, IgM, or an Fc fragment of an immunoglobulin.

4. The method of claim 3, wherein said Fc-containing polypeptide is an Fc fragment of an immunoglobulin.

5. The method of claim 1, wherein said Fc-containing polypeptide is derived from human, bovine, goat or murine immunoglobulin.

6. The method of claim 1, wherein said detecting comprises the step of amplifying an HCV nucleic acid.

7. The method of claim 6, wherein said nucleic acid is an RNA molecule, said amplifying comprises RT-PCR.

8. The method of claim 7, wherein said reverse transcribed nucleic acid is detected by electrophoretic separation.

9. The method of claim 7, wherein said reverse transcribed nucleic acid is integrally labeled with signal generating compound.

10. The method of claim 9, wherein said signal generating compound is a radioactive or fluorometric label.

11. The method of claim 1, wherein said detecting comprises the step of contacting said bound HCV with an antibody that binds immunologically to HCV.

12. The method of claim 11, wherein said first antibody is detected by a second antibody that binds to said first antibody.

13. The method of claim 11, wherein said antibody is labeled with signal generating compound.

14. The method of claim 13, wherein said signal generating compound is an enzyme.

15. The method of claim 14, wherein said enzyme is urease, glucose oxidase, alkaline phosphatase or hydrogen peroxidase.

16. The method of claim 13, wherein said signal generating compound is a fluorescent label.

17. The method of claim 13, wherein said signal generating compound is a radiolabel.

18. The method of claim 17, wherein said second antibody is labeled with a generating compound.

19. The method of claim 1, wherein said Fc-containing polypeptide is bound to a support.

20. The method of claim 19, wherein said support is a plate well, test tube, a dipstick, a column or a bead.

* * * * *

UNITED STATES PATENT AND TRADEMARK OFFICE
CERTIFICATE OF CORRECTION

PATENT NO.    :   5,846,735
DATED         :   December 8, 1998
INVENTOR(S)   :   Stapleton et al.

It is certified that error appears in the above-identified patent and that said Letters Patent is hereby corrected as shown below:

In claim 11, column 32, line 57, delete "an", and insert the following therefor: -- a first --.

In claim 13, column 32, line 62, after 'said', insert the following -- first --.

In claim 18, cloumn 33, line 6, after 'a', insert the following -- signal --.

Signed and Sealed this

Twenty-third Day of March, 1999

Attest:

Q. TODD DICKINSON

*Attesting Officer*    *Acting Commissioner of Patents and Trademarks*